(12) United States Patent
Scheller et al.

(10) Patent No.: US 9,364,371 B2
(45) Date of Patent: *Jun. 14, 2016

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US); Justin M Raney, O'Fallon, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/953,393

(22) Filed: Nov. 29, 2015

(65) Prior Publication Data

US 2016/0074223 A1 Mar. 17, 2016

Related U.S. Application Data

(63) Continuation of application No. 13/972,989, filed on Aug. 22, 2013, now Pat. No. 9,226,794.

(51) Int. Cl.
*A61B 18/18* (2006.01)
*A61F 9/008* (2006.01)
(Continued)

(52) U.S. Cl.
CPC ............ *A61F 9/00821* (2013.01); *A61B 18/22* (2013.01); *A61B 1/00158* (2013.01); *A61B 2017/00318* (2013.01); *A61B 2017/00367* (2013.01); *A61B 2018/0091* (2013.01); *A61B 2018/2238* (2013.01); *A61F 9/008* (2013.01);
(Continued)

(58) Field of Classification Search
CPC ............... A61B 2018/2238; A61B 2018/0091; A61F 9/008; A61F 9/00821
USPC .......................................................... 606/16
See application file for complete search history.

(56) References Cited

U.S. PATENT DOCUMENTS 5,190,050 A 3/1993 Nitzsche
5,355,871 A 10/1994 Hurley et al.
(Continued)

FOREIGN PATENT DOCUMENTS

EP         0900547 B1       3/1999
NL    WO 2013/133717       9/2013
WO    WO 2006/091597 A1   8/2006

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Lynsey Crandall
*Assistant Examiner* — Sebastian X Lukjan
(74) *Attorney, Agent, or Firm* — Kevin P. Rollins

(57) ABSTRACT

A steerable laser probe may include a handle having a handle distal end and a handle proximal end, an actuation control of the handle, a housing tube having a housing tube distal end and a housing tube proximal end, a first housing tube portion having a first stiffness, a second housing tube portion having a second stiffness, an optic fiber disposed within an inner portion of the handle and the housing tube, and a cable disposed within the housing tube and the actuation control. A rotation of the actuation control may be configured to gradually curve the housing tube and the optic fiber. A rotation of the actuation control may be configured to gradually straighten the housing tube and the optic fiber.

20 Claims, 16 Drawing Sheets

(51) Int. Cl.
    *A61B 18/22*     (2006.01)
    *A61B 1/00*     (2006.01)
    *A61B 18/00*     (2006.01)
    *A61B 17/00*     (2006.01)

(52) U.S. Cl.
    CPC ......... *A61F 9/00802* (2013.01); *A61F 9/00823* (2013.01)

(56) References Cited

U.S. PATENT DOCUMENTS

| | | |
|---|---|---|
| 5,381,782 A | 1/1995 | DeLaRama et al. |
| 5,439,000 A | 8/1995 | Gunderson et al. |
| 5,454,794 A | 10/1995 | Narciso et al. |
| 5,520,222 A | 5/1996 | Chikama |
| 5,855,577 A | 1/1999 | Murphy-Chutorian et al. |
| 6,123,699 A | 9/2000 | Webster, Jr. |
| 6,126,654 A | 10/2000 | Giba et al. |
| 6,178,354 B1 | 1/2001 | Gibson |
| 6,198,974 B1 | 3/2001 | Webster, Jr. |
| 6,488,695 B1 | 12/2002 | Hickingbotham |
| 6,505,530 B2 | 1/2003 | Adler et al. |
| 6,530,913 B1 | 3/2003 | Giba et al. |
| 6,533,772 B1 | 3/2003 | Sherts et al. |
| 6,551,302 B1 | 4/2003 | Rosinko et al. |
| 6,572,608 B1 | 6/2003 | Lee et al. |
| 6,620,153 B2 | 9/2003 | Mueller et al. |
| 6,730,076 B2 | 5/2004 | Hickingbotham |
| 6,863,668 B2 | 3/2005 | Gillespie et al. |
| 6,984,230 B2 | 1/2006 | Scheller et al. |
| 7,004,957 B1 | 2/2006 | Dampney et al. |
| 7,303,533 B2 | 12/2007 | Johansen et al. |
| 7,402,158 B2 | 7/2008 | Scheller et al. |
| 7,632,242 B2 | 12/2009 | Griffin et al. |
| 7,766,904 B2 | 8/2010 | Mc Gowan, Sr. et al. |
| 8,038,692 B2 | 10/2011 | Valencia et al. |
| 8,075,553 B2 | 12/2011 | Scheller et al. |
| 8,197,468 B2 | 6/2012 | Scheller et al. |
| 8,840,605 B2 | 9/2014 | Scheller et al. |
| 8,840,607 B2 | 9/2014 | Scheller et al. |
| 8,951,245 B2 | 2/2015 | Scheller et al. |
| 8,968,277 B2 | 3/2015 | Scheller et al. |
| 9,023,019 B2 | 5/2015 | Scheller et al. |
| 9,023,020 B2 | 5/2015 | Scheller et al. |
| 9,039,686 B2 | 5/2015 | Scheller et al. |
| 9,089,399 B2 | 7/2015 | Scheller et al. |
| 9,107,682 B2 | 8/2015 | Scheller et al. |
| 9,113,995 B2 | 8/2015 | Scheller et al. |
| 9,119,702 B2 | 9/2015 | Scheller et al. |
| 2003/0171762 A1 | 9/2003 | Forchette et al. |
| 2004/0181138 A1 | 9/2004 | Hindricks et al. |
| 2004/0249367 A1 | 12/2004 | Saadat et al. |
| 2005/0054900 A1 | 3/2005 | Mawn et al. |
| 2005/0157985 A1 | 7/2005 | McGowan, Sr. et al. |
| 2005/0234437 A1 | 10/2005 | Baxter et al. |
| 2005/0272975 A1 | 12/2005 | McWeeney et al. |
| 2005/0277874 A1 | 12/2005 | Selkee |
| 2006/0129175 A1 | 6/2006 | Griffin et al. |
| 2006/0178674 A1 | 8/2006 | McIntyre |
| 2007/0185514 A1 | 8/2007 | Kirchhevel |
| 2007/0260231 A1 | 11/2007 | Rose et al. |
| 2008/0132761 A1 | 6/2008 | Sonnenschein et al. |
| 2009/0018993 A1 | 1/2009 | McCool et al. |
| 2009/0163943 A1 | 6/2009 | Cavanaugh et al. |
| 2009/0187170 A1 | 7/2009 | Auld et al. |
| 2009/0312750 A1 | 12/2009 | Spaide |
| 2010/0004642 A1 | 1/2010 | Lumpkin |
| 2010/0191224 A1 | 7/2010 | Butcher |
| 2010/0268234 A1 | 10/2010 | Aho et al. |
| 2011/0028947 A1 | 2/2011 | Scheller et al. |
| 2012/0116361 A1 | 5/2012 | Hanlon et al. |
| 2012/0245569 A1 | 9/2012 | Papac et al. |
| 2013/0035551 A1 | 2/2013 | Yu et al. |
| 2013/0060240 A1 | 3/2013 | Scheller et al. |
| 2013/0071507 A1 | 3/2013 | Scheller et al. |
| 2013/0090635 A1 | 4/2013 | Mansour |
| 2013/0096541 A1 | 4/2013 | Scheller et al. |
| 2013/0116671 A1 | 5/2013 | Scheller et al. |
| 2013/0150838 A1 | 6/2013 | Scheller et al. |
| 2013/0165910 A1 | 6/2013 | Scheller et al. |
| 2013/0261610 A1 | 10/2013 | LaConte et al. |
| 2013/0281994 A1 | 10/2013 | Scheller et al. |
| 2013/0304043 A1 | 11/2013 | Scheller et al. |
| 2013/0304048 A1 | 11/2013 | Scheller et al. |
| 2014/0005642 A1 | 1/2014 | Scheller et al. |
| 2014/0039471 A1 | 2/2014 | Scheller et al. |
| 2014/0039472 A1 | 2/2014 | Scheller et al. |
| 2014/0039475 A1 | 2/2014 | Scheller et al. |
| 2014/0046307 A1 | 2/2014 | Scheller et al. |
| 2014/0052115 A1 | 2/2014 | Zeid et al. |
| 2014/0066907 A1 | 3/2014 | Scheller et al. |
| 2014/0066912 A1 | 3/2014 | Scheller et al. |
| 2014/0074073 A1 | 3/2014 | Scheller et al. |
| 2014/0074079 A1 | 3/2014 | Scheller et al. |
| 2014/0088572 A1 | 3/2014 | Scheller et al. |
| 2014/0088576 A1 | 3/2014 | Scheller et al. |
| 2014/0107628 A1 | 4/2014 | Scheller et al. |
| 2014/0107629 A1 | 4/2014 | Scheller et al. |
| 2015/0038950 A1 | 2/2015 | Scheller et al. |

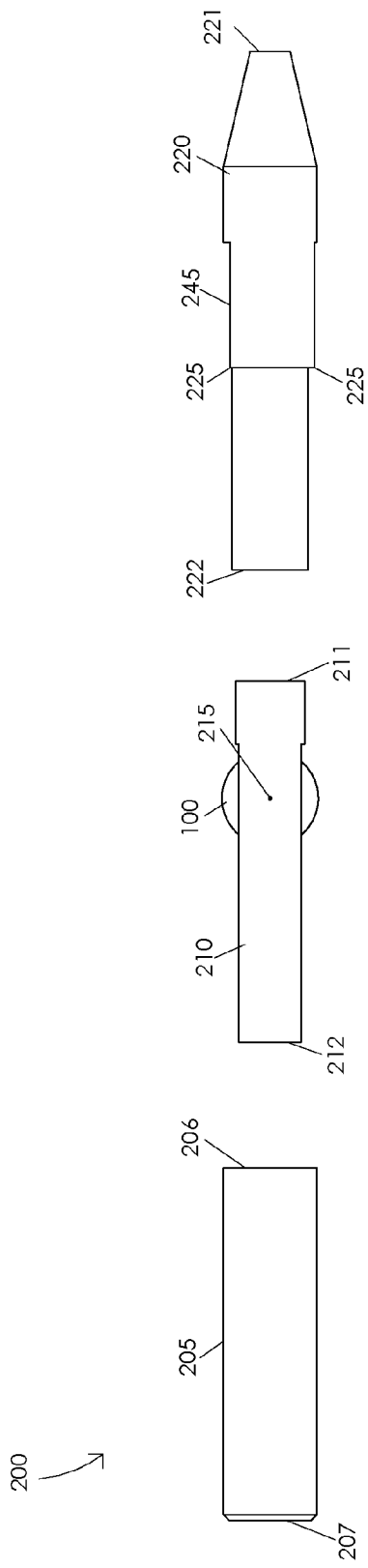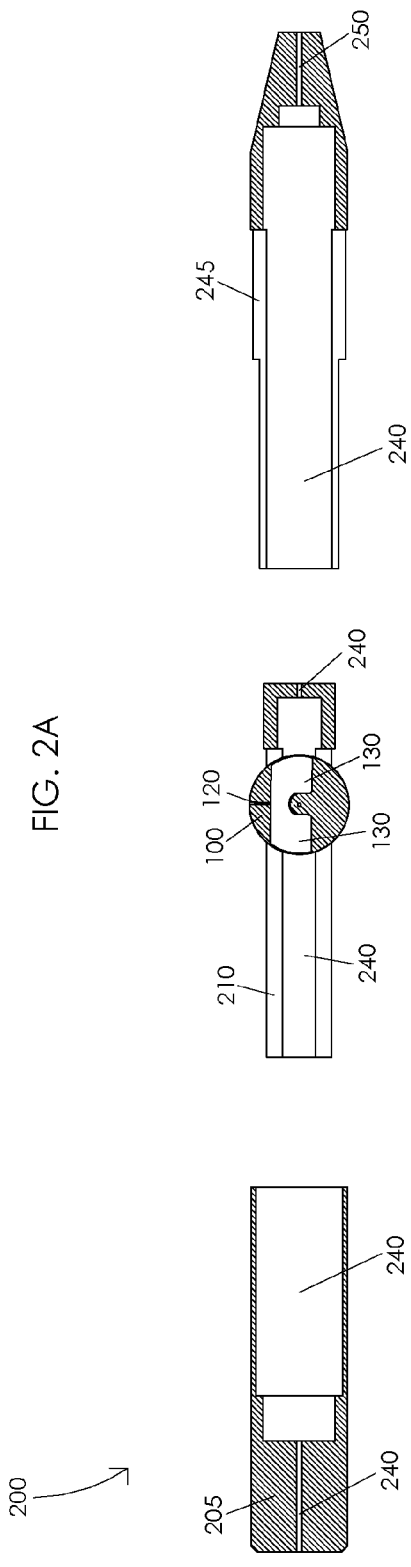
FIG. 2A
FIG. 2B

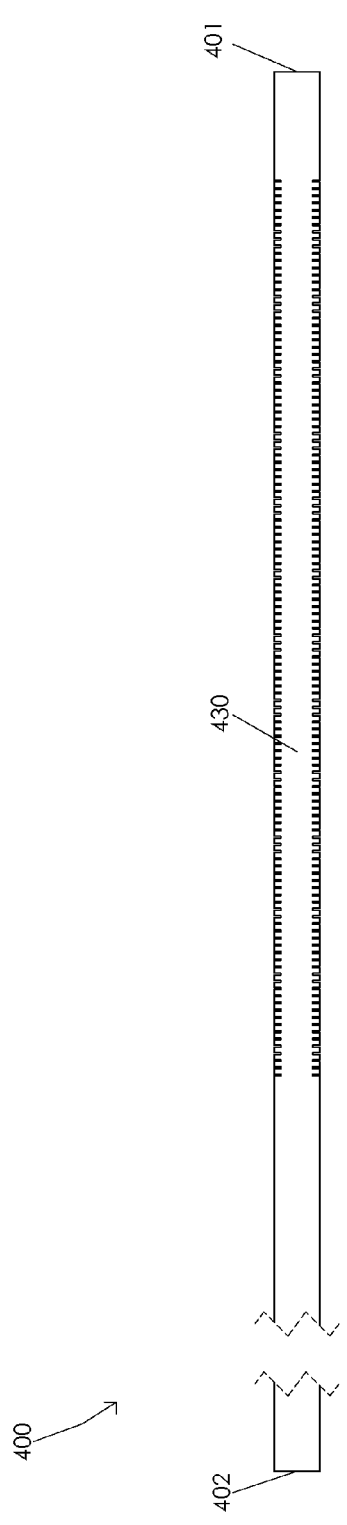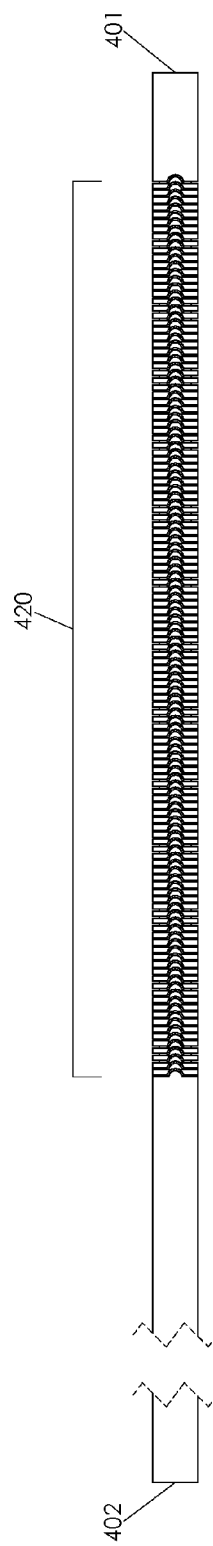
FIG. 4B
FIG. 4A

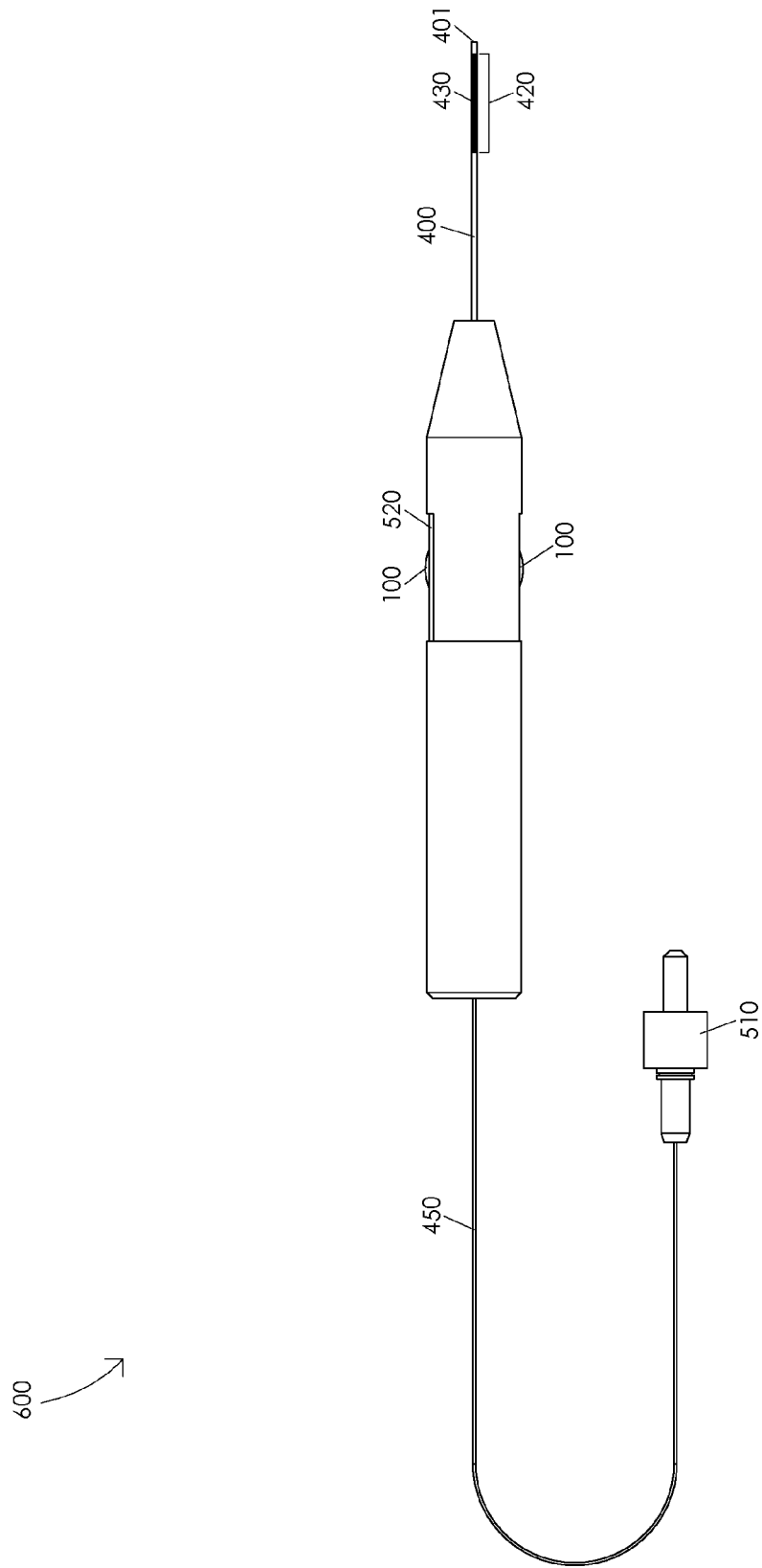

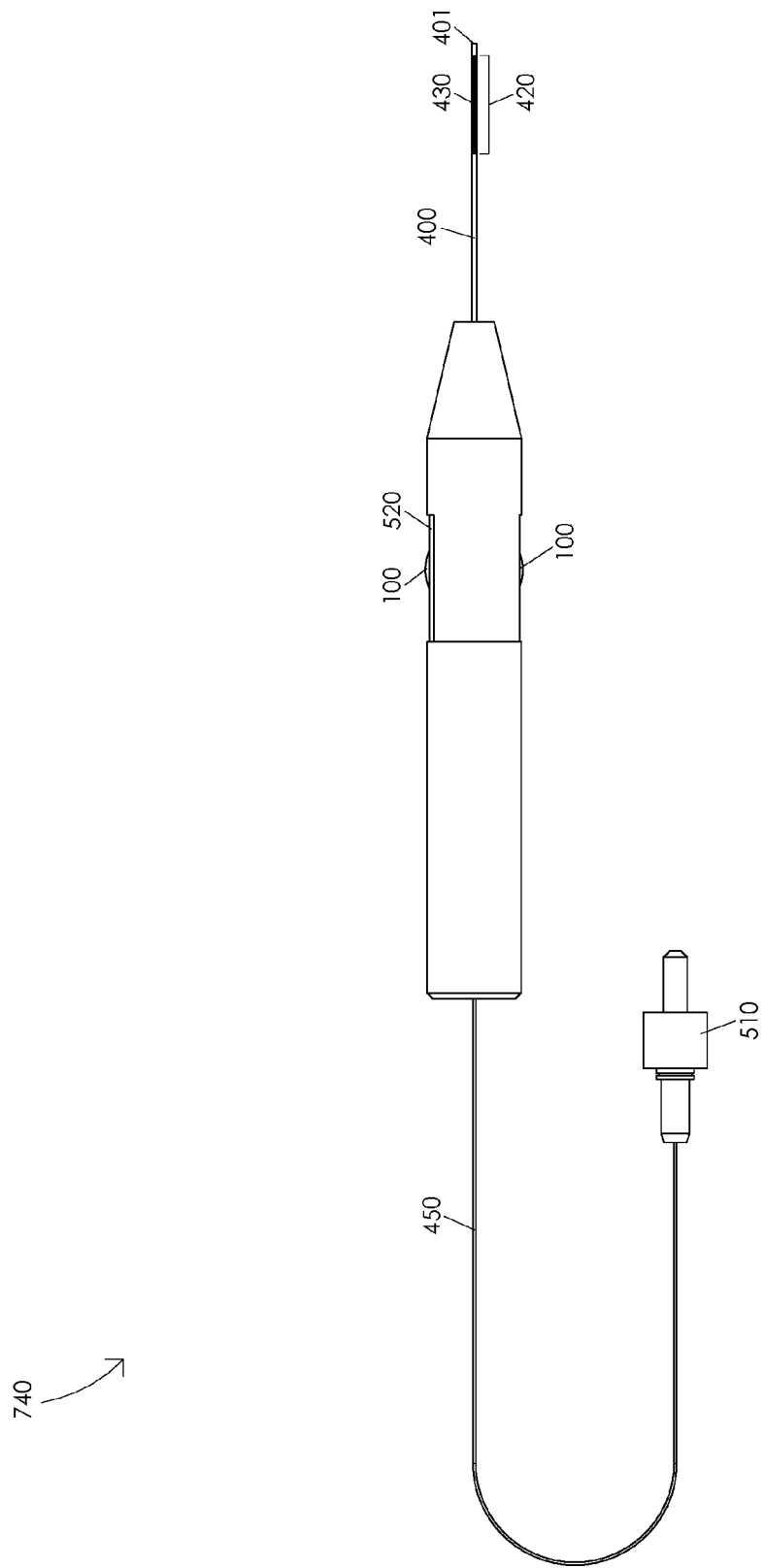

STEERABLE LASER PROBE

CROSS-REFERENCE TO RELATED APPLICATIONS

This Application is a continuation of prior application Ser. No. 13/972,989 filed Aug. 22, 2013.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle having a handle distal end and a handle proximal end, an actuation control of the handle, a housing tube having a housing tube distal end and a housing tube proximal end, a first housing tube portion having a first stiffness, a second housing tube portion having a second stiffness, an optic fiber disposed within an inner portion of the handle and the housing tube, and a cable disposed within the housing tube and the actuation control. Illustratively, a rotation of the actuation control may be configured to gradually curve the housing tube. In one or more embodiments, a gradual curving of the housing tube may be configured to gradually curve the optic fiber. Illustratively, a rotation of the actuation control may be configured to gradually straighten the housing tube. In one or more embodiments, a gradual straightening of the housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 2A and 2B are schematic diagrams illustrating an exploded view of a handle assembly;

FIGS. 4A, 4B, and 4C are schematic diagrams illustrating a housing tube;

FIGS. 6A, 6B, 6C, 6D, and 6E are schematic diagrams illustrating a gradual curving of an optic fiber;

FIGS. 7A, 7B, 7C, 7D, and 7E are schematic diagrams illustrating a gradual straightening of an optic fiber.

DETAILED DESCRIPTION OF AN ILLUSTRATIVE EMBODIMENT

Figure 1A:
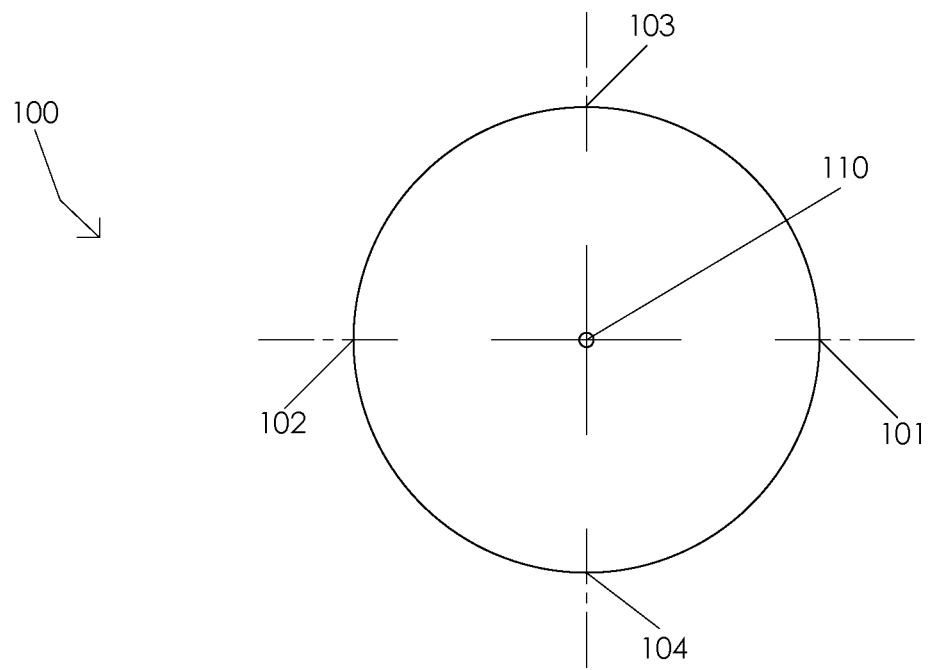
FIGS. 1A and 1B are schematic diagrams illustrating an actuation control.
Figure 1B:
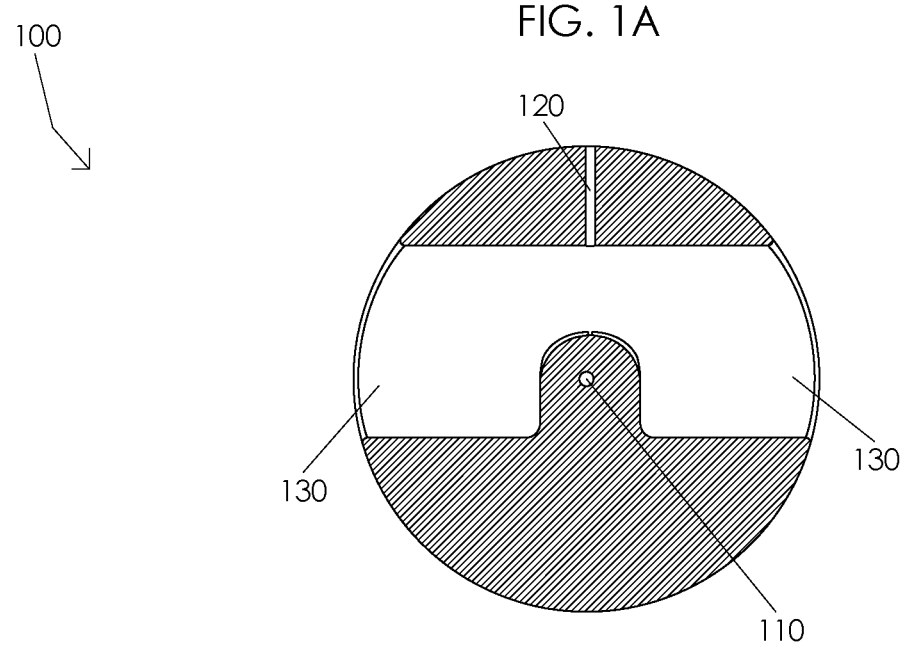

FIGS. 1A and 1B are schematic diagrams illustrating an actuation control 100. FIG. 1A illustrates a side view of an actuation control 100. Illustratively, actuation control 100 may comprise an actuation control distal end 101, an actuation control proximal end 102, an actuation control anterior end 103, and an actuation control posterior end 104. FIG. 1B illustrates a cross-sectional view of an actuation control 100. In one or more embodiments, actuation control 100 may comprise a fixation pin guide 110, a cable housing 120, and an actuation chamber 130. Illustratively, actuation control 100 may be manufactured from any suitable material, e.g., polymers, metals, metal alloys, etc., or from any combination of suitable materials.

FIGS. 2A and 2B are schematic diagrams illustrating an exploded view of a handle assembly 200. FIG. 2A illustrates a side view of a handle assembly 200. In one or more embodiments, handle assembly 200 may comprise a handle end cap 205 having a handle end cap distal end 206 and a handle end cap proximal end 207, an actuation control mount 210 having an actuation control mount distal end 211 and an actuation control mount proximal end 212, an actuation control 100, a fixation pin 215, a handle base 220 having a handle base distal end 221 and a handle base proximal end 222, and a handle end cap interface 225. Illustratively, actuation control 100 may be disposed within actuation control mount 210. In one or more embodiments, fixation pin 215 may be configured to fix actuation control 100 within actuation control mount 210, e.g., fixation pin 215 may be disposed within a portion of actuation control mount 210 and within a portion of actuation control 100. Illustratively, fixation pin 215 may be disposed within actuation control mount 210 and fixation pin guide 110. In one or more embodiments, actuation control 100 may be rotated about fixation pin 215, e.g., a surgeon may rotate actuation control 100 within actuation control mount 210 by applying a force to a portion of actuation control 100.

FIG. 2B illustrates a cross-sectional view of a handle assembly 200. Illustratively, handle assembly 200 may comprise a handle inner portion 240, an auto-fixing component housing 245, and a housing tube housing 250. In one or more embodiments, actuation control 100 may be oriented wherein a portion of actuation chamber 130 may be disposed within a portion of handle inner portion 240. Illustratively, handle end cap 205, actuation control mount 210, and handle base 220 may be manufactured from any suitable material, e.g., polymers, metals, metal alloys, etc., or from any combination of suitable materials.

Figure 3A:
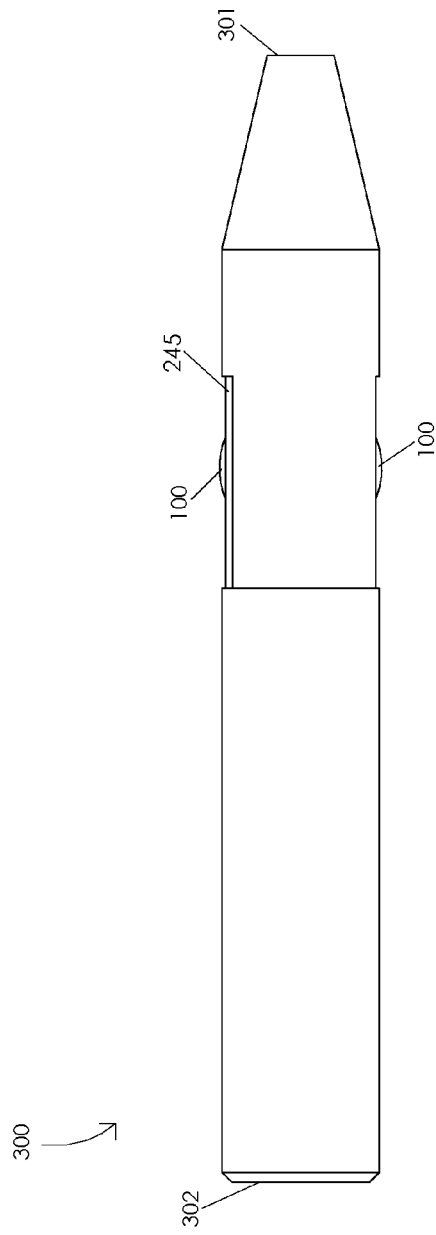
FIGS. 3A and 3B are schematic diagrams illustrating a handle.
Figure 3B:
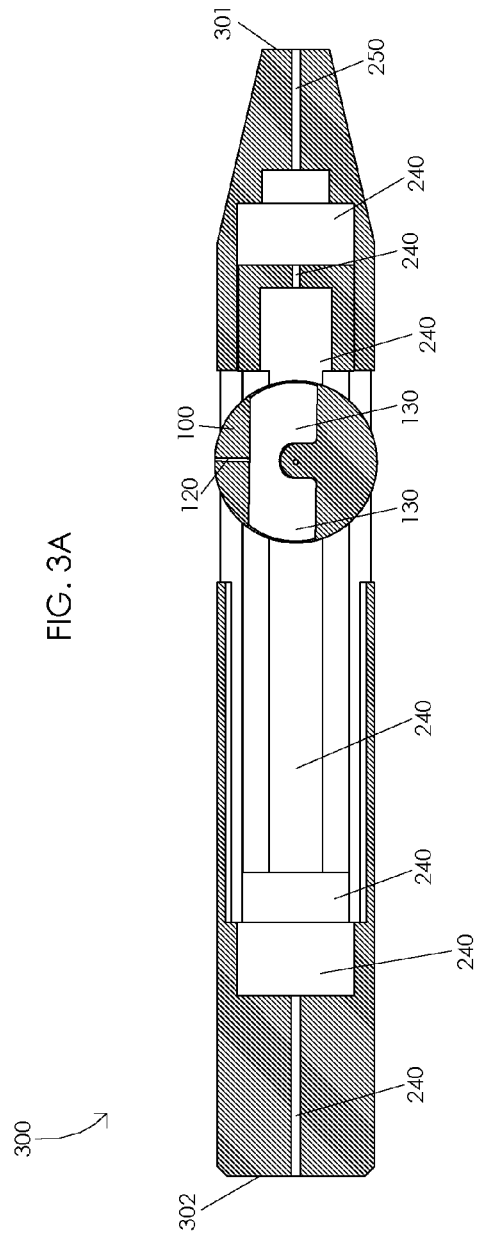

FIGS. 3A and 3B are schematic diagrams illustrating a handle 300. FIG. 3A illustrates a side view of a handle 300. Illustratively, handle 300 may comprise a handle distal end 301 and a handle proximal end 302. In one or more embodiments, handle distal end 301 may comprise a portion of handle base 220, e.g., handle distal end 301 may comprise handle base distal end 221. Illustratively, handle proximal end 302 may comprise a portion of end cap 205, e.g., handle proximal end 302 may comprise handle end cap proximal end 207.

FIG. 3B illustrates a cross-sectional view of a handle 300. In one or more embodiments, actuation control mount 210 may be disposed within handle end cap 205 and handle base 220. Illustratively, actuation control mount 210 may be disposed within handle end cap 205 and handle base 220 wherein a portion of actuation control 100 may be adjacent to a portion of auto-fixing component housing 245. In one or more embodiments, a portion of handle base 220 may be disposed within a portion of handle end cap 205, e.g., handle base proximal end 222 may be disposed within handle end cap 205. In one or more embodiments, a portion of handle base 220 may be disposed within handle end cap 205 wherein handle end cap interface 225 may be configured to interface with a portion of handle end cap 205, e.g., handle end cap interface 225 may be configured to interface with handle end cap distal end 206. Illustratively, a portion of handle base 220 may be fixed within handle end cap 205, e.g., by an adhesive or any suitable fixation means. In one or more embodiments, a portion of handle base 220 may be fixed within handle end cap 205 by a press fit, a setscrew, a weld, etc. Illustratively, handle base 220 and handle end cap 205 may be manufactured as a single unit.

Figure 4C:
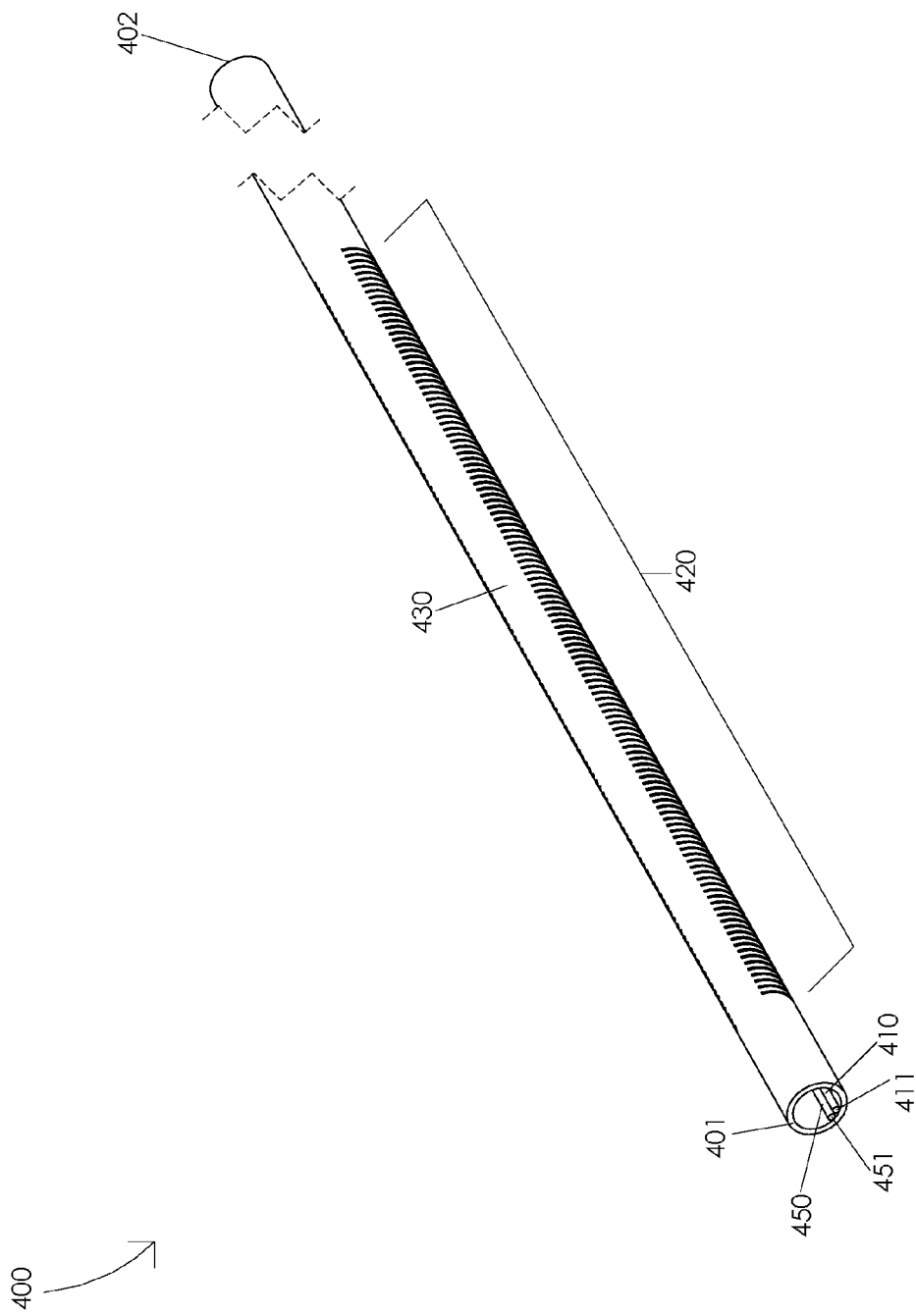

FIGS. 4A, 4B, and 4C are schematic diagrams illustrating a housing tube 400. In one or more embodiments, housing tube 400 may comprise a housing tube distal end 401 and a housing tube proximal end 402. Housing tube 400 may be manufactured from any suitable material, e.g., polymers, metals, metal alloys, etc., or from any combination of suitable materials. Illustratively, housing tube 400 may be manufactured with dimensions configured for microsurgical procedures, e.g., ophthalmic surgical procedures. FIG. 4A illustrates a housing tube 400 oriented to illustrate a first housing tube portion 420. Illustratively, first housing tube portion 420 may have a first stiffness. FIG. 4B illustrates a housing tube 400 oriented to illustrate a second housing tube portion 430. Illustratively, second housing tube portion 430 may have a second stiffness. In one or more embodiments, the second stiffness may be greater than the first stiffness. Illustratively, first housing tube portion 420 may comprise a first material having a first stiffness. In one or more embodiments, second housing tube portion 430 may comprise a second material having a second stiffness. Illustratively, the second stiffness may be greater than the first stiffness.

In one or more embodiments, housing tube 400 may comprise a non-uniform inner diameter or a non-uniform outer diameter, e.g., to vary a stiffness of one or more portions of housing tube 400. Illustratively, a first housing tube portion 420 may comprise a first inner diameter of housing tube 400 and a second housing tube portion 430 may comprise a second inner diameter of housing tube 400. In one or more embodiments, the first inner diameter of housing tube 400 may be larger than the second inner diameter of housing tube 400. Illustratively, a first housing tube portion 420 may comprise a first outer diameter of housing tube 400 and a second housing tube portion 430 may comprise a second outer diameter of housing tube 400. In one or more embodiments, the first outer diameter of housing tube 400 may be smaller than the second outer diameter of housing tube 400.

In one or more embodiments, first housing tube portion 420 may comprise one or more apertures configured to produce a first stiffness of first housing tube portion 420. Illustratively, second housing tube portion 430 may comprise a solid portion of housing tube 400 having a second stiffness. In one or more embodiments, the second stiffness may be greater than the first stiffness. Illustratively, first housing tube portion 420 may comprise one or more apertures configured to produce a first stiffness of first housing tube portion 420. In one or more embodiments, second housing tube portion 430 may comprise one or more apertures configured to produce a second stiffness of second housing tube portion 430. Illustratively, the second stiffness may be greater than the first stiffness.

In one or more embodiments, first housing tube portion 420 may comprise a plurality of slits configured to separate one or more solid portions of housing tube 400. Illustratively, a plurality of slits may be cut, e.g., laser cut, into first housing tube portion 420. In one or more embodiments, first housing tube portion 420 may comprise a plurality of slits configured to minimize a force of friction between housing tube 400 and a cannula, e.g., as housing tube 400 is inserted into the cannula or as housing tube 400 is extracted from the cannula. For example, each slit of the plurality of slits may comprise one or more arches configured to minimize a force of friction between housing tube 400 and a cannula.

FIG. 4C illustrates an angled view of housing tube 400. Illustratively, an optic fiber 450 may be disposed within housing tube 400. In one or more embodiments, optic fiber 450 may comprise an optic fiber distal end 451 and an optic fiber proximal end 452. Illustratively, optic fiber 450 may be configured to transmit light, e.g., laser light, illumination light, etc. In one or more embodiments, optic fiber 450 may be disposed within housing tube 400 wherein optic fiber distal end 451 may be adjacent to housing tube distal end 401. Illustratively, optic fiber 450 may be disposed within housing tube 400 wherein a portion of optic fiber 450 may be adjacent to a portion of first housing tube portion 420. In one or more embodiments, a portion of optic fiber 450 may be fixed to an inner portion of housing tube 400, e.g., by an adhesive or any suitable fixation means.

Illustratively, a cable 410 may be disposed in housing tube 400. In one or more embodiments, a cable 410 may comprise a cable distal end 411 and a cable proximal end 412. Illustratively, cable 410 may be disposed in housing tube 400 wherein cable distal end 411 may be adjacent to housing tube distal end 401. In one or more embodiments, cable 410 may be disposed in housing tube 400 wherein a portion of cable 410 may be adjacent to a portion of first housing tube portion 420. Illustratively, a portion of cable 410 may be fixed to a portion of housing tube 400, e.g., cable distal end 411 may be fixed to a portion of housing tube 400. In one or more embodiments, a portion of cable 410 may be fixed to a portion of housing tube 400, e.g., by an adhesive or any suitable fixation means. Illustratively, a portion of cable 410 may be fixed to a portion of housing tube 400 by a weld, a press fit, a loop, a tie, etc.

Figure 5:
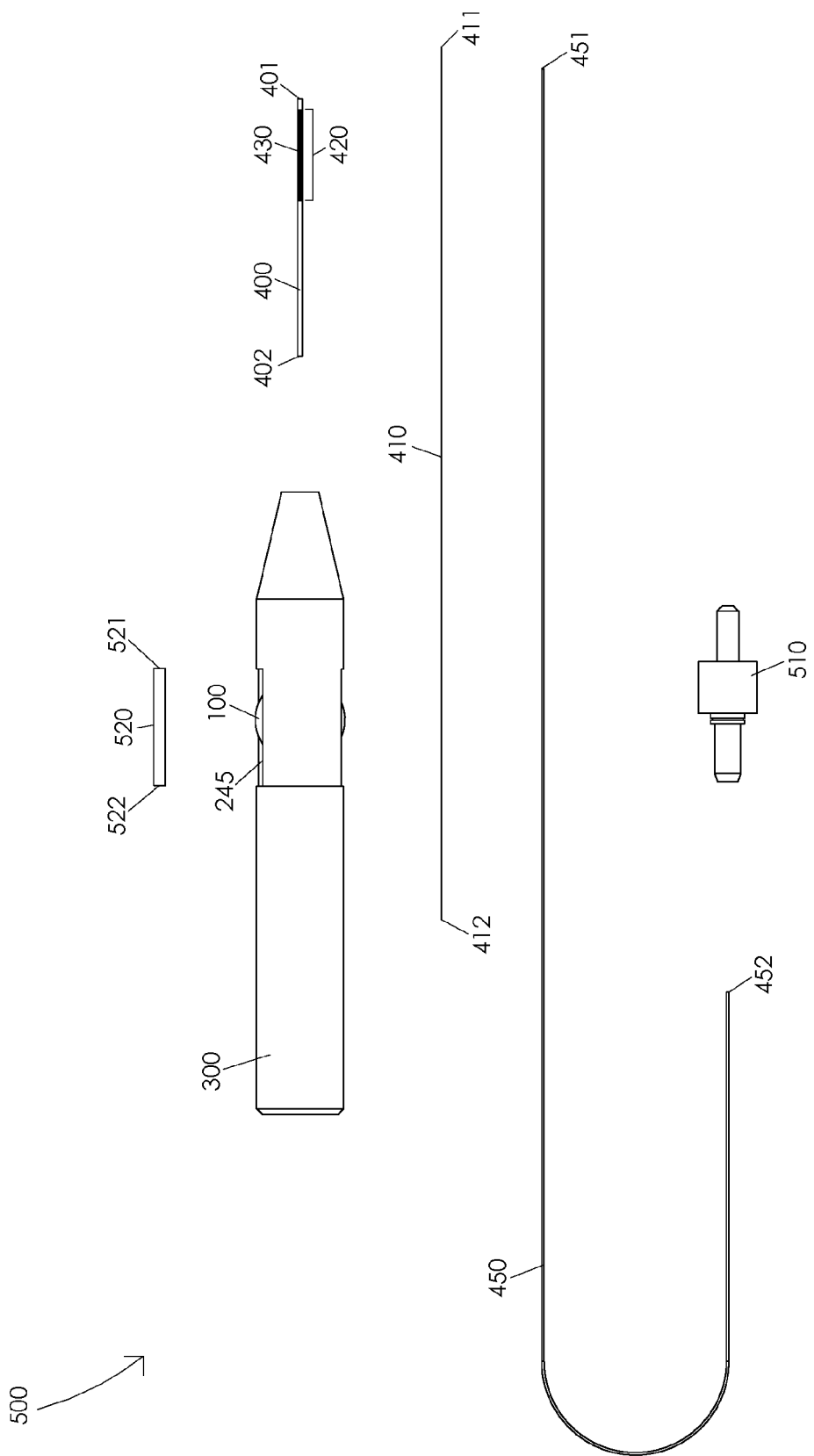
FIG. 5 is a schematic diagram illustrating an exploded view of a steerable laser probe assembly.

FIG. 5 is a schematic diagram illustrating an exploded view of a steerable laser probe assembly 500. In one or more embodiments, a steerable laser probe assembly 500 may comprise a handle 300 having a handle distal end 301 and a handle proximal end 302, a housing tube 400 having a housing tube distal end 401 and a housing tube proximal end 402, a cable 410 having a cable distal end 411 and a cable proximal end 412, an optic fiber 450 having an optic fiber distal end 451 and an optic fiber proximal end 452, an auto-fixing component 520 having an auto-fixing component distal end 521 and an auto-fixing component proximal end 522, and a light source interface 510. Illustratively, light source interface 510 may be configured to interface with optic fiber 450, e.g., at optic fiber proximal end 452. In one or more embodiments, light source interface 510 may comprise a standard light source connecter, e.g., an SMA connector.

Illustratively, a portion of housing tube 400 may be disposed within a portion of handle 300, e.g., housing tube proximal end 402 may be disposed within a portion of handle 300. In one or more embodiments, a portion of housing tube 400 may be disposed within a portion of handle base 220, e.g., housing tube proximal end 402 may be disposed in housing tube housing 250. Illustratively, a portion of housing tube 400 may be fixed within a portion of handle 300, e.g., housing tube proximal end 402 may be fixed within housing tube housing 250. In one or more embodiments, a portion of housing tube 400 may be fixed within housing tube housing 250, e.g., by an adhesive or any suitable fixation means. For example, a portion of housing tube 400 may be fixed within housing tube housing 250 by a press fit, a set screw, etc.

Illustratively, optic fiber 450 may be disposed within handle inner portion 240, actuation chamber 130, housing tube housing 250, and housing tube 400. In one or more embodiments, optic fiber 450 may be disposed within housing tube 400 wherein optic fiber distal end 451 may be adjacent to housing tube distal end 401. Illustratively, a portion of optic fiber 450 may be fixed to a portion of housing tube 400, e.g., by an adhesive or any suitable fixation means. In one or more embodiments, cable 410 may be disposed within cable housing 120, actuation chamber 130, handle inner portion 240, housing tube housing 250, and housing tube 400. Illustratively, cable 410 may be disposed within housing tube 400 wherein cable distal end 411 may be adjacent to housing tube distal end 401. In one or more embodiments, cable 410 may be disposed within housing tube 400 wherein a portion of cable 410 may be adjacent to a portion of first housing tube portion 420. Illustratively, a portion of cable 410 may be fixed to a portion of housing tube 400, e.g., by an adhesive or any suitable fixation means. For example, a portion of cable 410 may be fixed to a portion of housing tube 400 by a weld, a press fit, a loop, a tie, etc. In one or more embodiments, a portion of cable 410 may be fixed within cable housing 120, e.g., by an adhesive or any suitable fixation means. For example, a portion of cable 410 may be fixed within cable housing 120 by a weld, a press fit, a loop, a tie, etc. Illustratively, a first portion of cable 410 may be fixed to a portion of housing tube 400 and a second portion of cable 410 may be fixed within cable housing 120. In one or more embodiments, cable distal end 411 may be fixed to a portion of housing tube 400. Illustratively, cable proximal end 412 may be fixed within cable housing 120.

In one or more embodiments, a surgeon may rotate actuation control 100 within handle inner portion 240, e.g., by applying a force to a portion of actuation control 100. Illustratively, actuation chamber 130 may be configured to prevent a contact between a portion of actuation control 100 and a portion of optic fiber 450, e.g., due to a rotation of actuation control 100. In one or more embodiments, a geometry of actuation chamber 130 may be configured to prevent a contact between a portion of actuation control 100 and a portion of optic fiber 450, e.g., due to a rotation of actuation control. Illustratively, a surgeon may rotate actuation control 100 about fixation pin 215, e.g., by applying a force to a portion of actuation control 100. In one or more embodiments, a rotation of actuation control 100 may be configured to retract cable 410 relative to housing tube 400. Illustratively, a refraction of cable 410 relative to housing tube 400 may be configured to apply a force to a portion of housing tube 400, e.g., a retraction of cable 410 relative to housing tube 400 may be configured to apply a force to first housing tube portion 420. In one or more embodiments, an application of a force to a portion of housing tube 400 may be configured to compress a portion of housing tube 400, e.g., an application of a force to a portion of housing tube 400 may be configured to compress first housing tube portion 420. Illustratively, a compression of a portion of housing tube 400 may be configured to cause housing tube 400 to gradually curve. In one or more embodiments, a gradual curving of housing tube 400 may be configured to gradually curve optic fiber 450. Illustratively, a rotation of actuation control 100 may be configured to gradually curve optic fiber 450.

In one or more embodiments, a rotation of actuation control 100 may be configured to extend cable 410 relative to housing tube 400. Illustratively, an extension of cable 410 relative to housing tube 400 may be configured to reduce a force applied to a portion of housing tube 400, e.g., an extension of cable 410 relative to housing tube 400 may be configured to reduce a force applied to first housing tube portion 420. In one or more embodiments, a reduction of a force applied to a portion of housing tube 400 may be configured to decompress a portion of housing tube 400, e.g., a reduction of a force applied to a portion of housing tube 400 may be configured to decompress first housing tube portion 420. Illustratively, a decompression of a portion of housing tube 400 may be configured to cause housing tube 400 to gradually straighten. In one or more embodiments, a gradual straightening of housing tube 400 may be configured to gradually straighten optic fiber 450. Illustratively, a rotation of actuation control 100 may be configured to gradually straighten optic fiber 450.

In one or more embodiments, auto-fixing component 520 may be disposed within auto-fixing component housing 245. Illustratively, auto-fixing component 520 may be fixed within auto-fixing component housing 245, e.g., by an adhesive or any suitable fixation means. In one or more embodiments, auto-fixing component 520 may be disposed within auto-fixing component housing 245 wherein a portion of auto-fixing component 520 may be adjacent to a portion of actuation control 100. Illustratively, auto-fixing component 520 may be configured to produce a magnetic field, e.g., auto-fixing component 520 may comprise a permanent magnet. In one or more embodiments, auto-fixing component 520 may comprise a ferromagnetic material, e.g., auto-fixing component 520 may comprise a ferrimagnetic material. Illustratively, actuation control 100 may be configured to produce a magnetic field, e.g., actuation control 100 may comprise a permanent magnetic. In one or more embodiments, actuation control 100 may comprise a ferromagnetic material, e.g., actuation control 100 may comprise a ferrimagnetic material.

Illustratively, auto-fixing component 520 may be configured to temporarily fix actuation control 100 in a rotational position within handle inner portion 240, e.g., a magnetic force attracting actuation control 100 to auto-fixing component 520 may be configured to hold actuation control 100 fixed in a rotational position within handle inner portion 240. In one or more embodiments, actuation control 100 may be configured to temporarily fix actuation control 100 in a rotational position within handle inner portion 240, e.g., a magnetic force attracting auto-fixing component 520 to actuation control 100 may be configured to temporarily hold actuation control 100 fixed in a rotational position within handle inner portion 240. Illustratively, both auto-fixing component 520 and actuation control 100 may be configured to temporarily fix actuation control 100 in a rotational position within handle inner portion 240, e.g., auto-fixing component 520 and actuation control 100 may both comprise permanent magnets having poles oriented to attract auto-fixing component 520 to actuation control 100 and to attract actuation control 100 to auto-fixing component 520.

In one or more embodiments, a surgeon may actuate actuation control 100 within handle inner portion 240, e.g., by applying a force to a portion of actuation control 100 until actuation control 100 is in a first desired rotational position within handle inner portion 240. Illustratively, the surgeon may then remove the force applied to actuation control 100 and perform a portion of a surgical procedure, e.g., actuation control 100 and auto-fixing component 520 may be configured to temporarily fix actuation control 100 in the first desired rotational position within handle inner portion 240. In one or more embodiments, the surgeon may actuate actuation control 100 within handle inner portion 240, e.g., by applying a force to a portion of actuation control 100 until actuation control 100 is in a second desired rotational position within handle inner portion 240. Illustratively, the surgeon may then remove the force applied to actuation control 100 and perform a portion of a surgical procedure, e.g., actuation control 100 and auto-fixing component 520 may be configured to temporarily fix actuation control 100 in the second desired rotational position within handle inner portion 240. In one or more embodiments, the surgeon may actuate actuation control 100 within handle inner portion 240, e.g., by applying a force to a portion of actuation control 100 until actuation control 100 is in a third desired rotational position within handle inner portion 240. Illustratively, the surgeon may then remove the force applied to actuation control 100 and perform a portion of a surgical procedure, e.g., actuation control 100 and auto-fixing component 520 may be configured to temporarily fix actuation control 100 in the third desired rotational position within handle inner portion 240. In one or more embodiments, actuation control 100 and auto-fixing component 520 may be configured to temporarily fix actuation control 100 in any desired rotational position within handle inner portion 240.

Figure 6B:
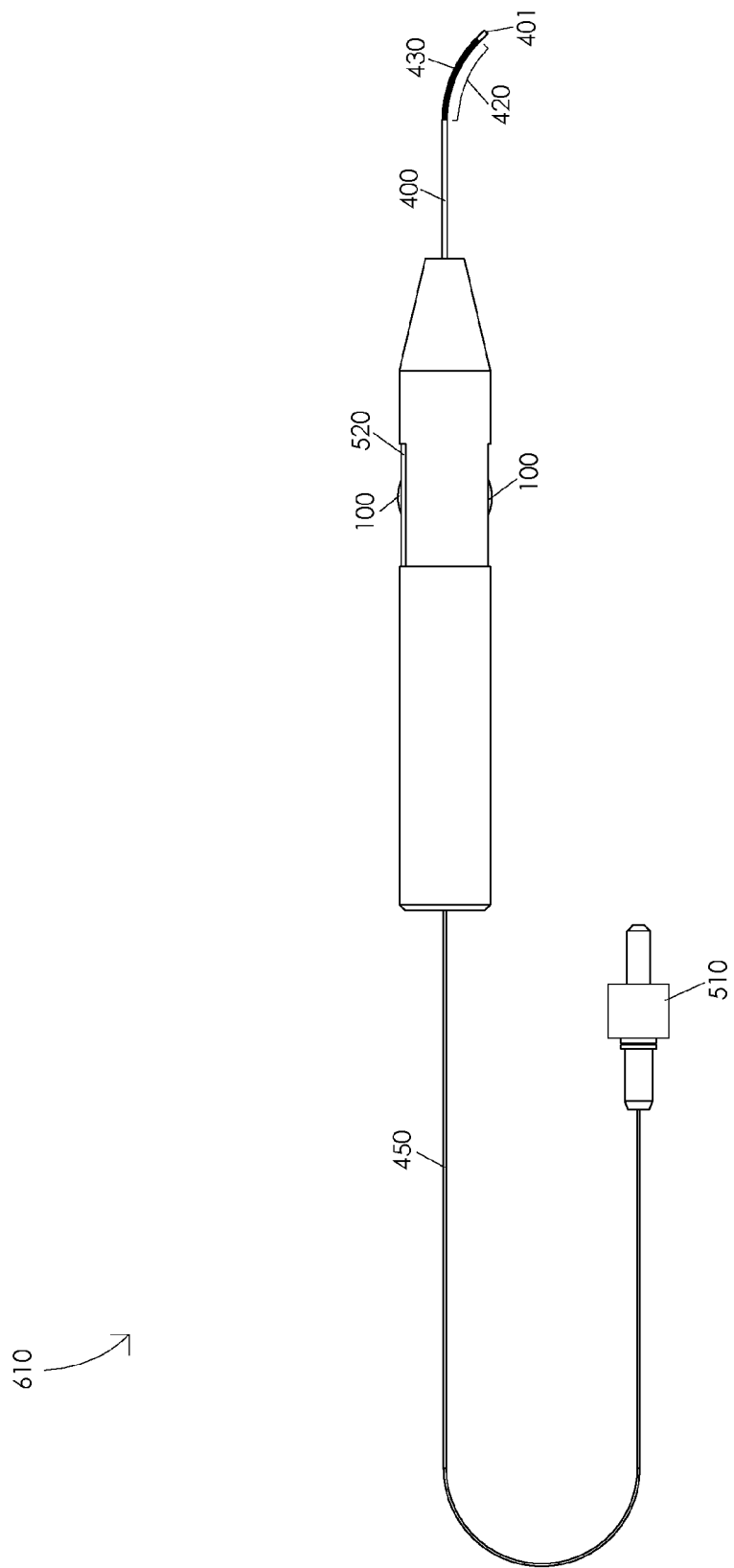

FIGS. 6A, 6B, 6C, 6D, and 6E are schematic diagrams illustrating a gradual curving of an optic fiber 450. FIG. 6A illustrates a straight optic fiber 600. In one or more embodiments, optic fiber 450 may comprise a straight optic fiber 600, e.g., when cable 410 is fully extended relative to housing tube 400. For example, optic fiber 450 may comprise a straight optic fiber 600, e.g., when first housing tube portion 420 is fully decompressed. Illustratively, a line tangent to optic fiber distal end 451 may be parallel to a line tangent to housing tube proximal end 402, e.g., when optic fiber 450 comprises a straight optic fiber 600. In one or more embodiments, actuation control 100 and autofixing component 520 may be configured to temporarily fix actuation control 100 in a first fixed rotational position within handle inner portion 240. Illustratively, optic fiber 450 may comprise a straight optic fiber 600, e.g., when actuation control 100 is fixed in the first fixed rotational position within handle inner portion 240.

FIG. 6B illustrates an optic fiber in a first curved position 610. In one or more embodiments, a rotation of actuation control 100 within handle inner portion 240 may be configured to gradually curve optic fiber 450 from a straight optic fiber 600 to an optic fiber in a first curved position 610. Illustratively, a rotation of actuation control 100 within handle inner portion 240 may be configured to retract cable 410 relative to housing tube 400. In one or more embodiments, a retraction of cable 410 relative to housing tube 400 may be configured to apply a force to a portion of housing tube 400, e.g., a retraction of cable 410 relative to housing tube 400 may be configured to apply a force to a portion of first housing tube portion 420. Illustratively, an application of a force to a portion of housing tube 400 may be configured to compress a portion of housing tube 400, e.g., an application of a force to a portion of housing tube 400 may be configured to compress a portion of first housing tube portion 420. In one or more embodiments, a compression of a portion of housing tube 400 may be configured to gradually curve housing tube 400. Illustratively, a gradual curving of housing tube 400 may be configured to gradually curve optic fiber 450, e.g., from a straight optic fiber 600 to an optic fiber in a first curved position 610. In one or more embodiments, a line tangent to optic fiber distal end 451 may intersect a line tangent to housing tube proximal end 402 at a first angle, e.g., when optic fiber 450 comprises an optic fiber in a first curved position 610. In one or more embodiments, the first angle may comprise any angle greater than zero degrees. For example, the first angle may comprise a 45 degree angle. Illustratively, actuation control 100 and auto-fixing component 520 may be configured to temporarily fix actuation control 100 in a second fixed rotational position within handle inner portion 240. In one or more embodiments, optic fiber 450 may comprise an optic fiber in a first curved position 610, e.g., when actuation control 100 is fixed in the second fixed rotational position within handle inner portion 240.

Figure 6C:
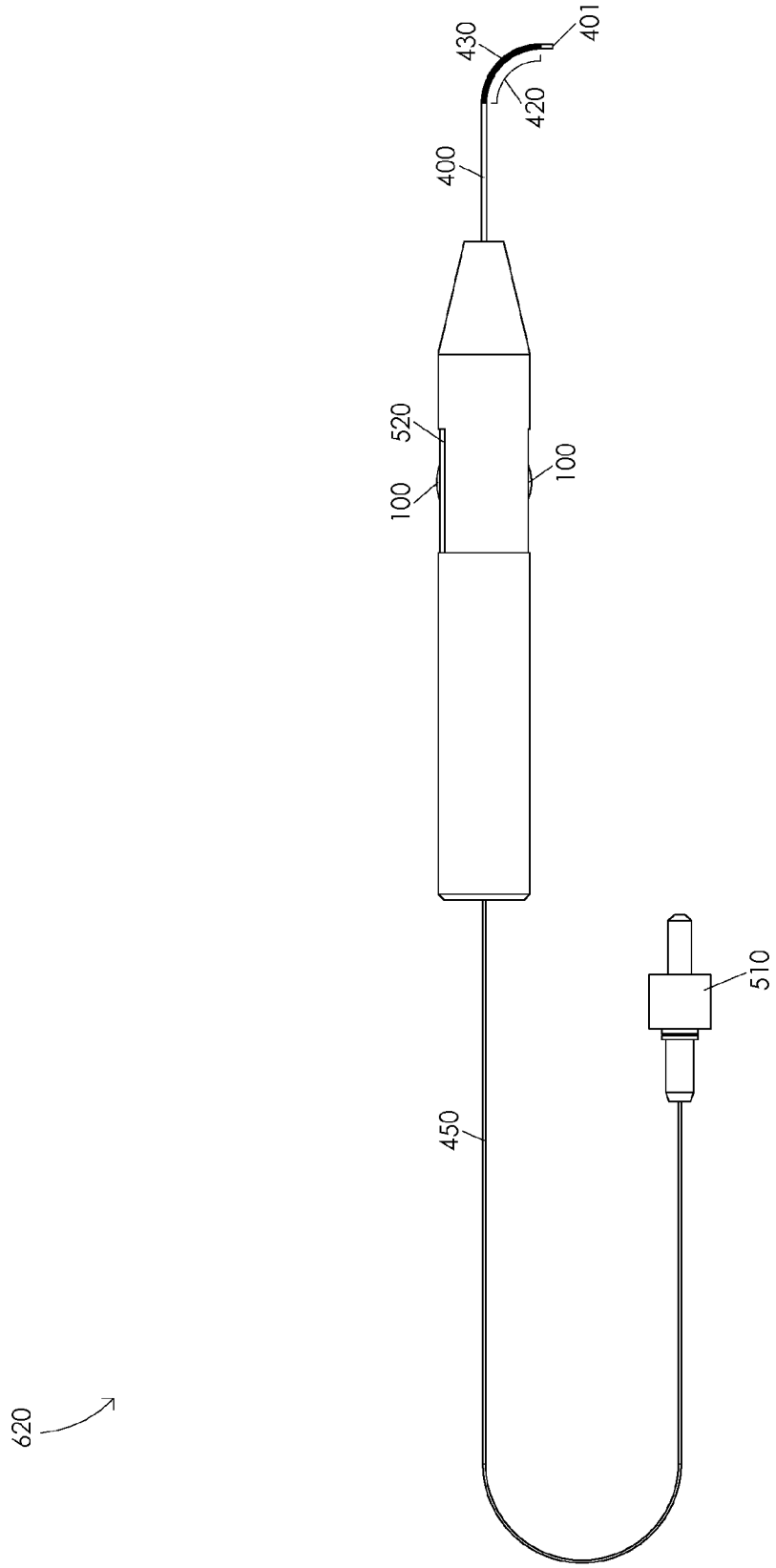

FIG. 6C illustrates an optic fiber in a second curved position 620. In one or more embodiments, a rotation of actuation control 100 within handle inner portion 240 may be configured to gradually curve optic fiber 450 from an optic fiber in a first curved position 610 to an optic fiber in a second curved position 620. Illustratively, a rotation of actuation control 100 within handle inner portion 240 may be configured to retract cable 410 relative to housing tube 400. In one or more embodiments, a retraction of cable 410 relative to housing tube 400 may be configured to apply a force to a portion of housing tube 400, e.g., a retraction of cable 410 relative to housing tube 400 may be configured to apply a force to a portion of first housing tube portion 420. Illustratively, an application of a force to a portion of housing tube 400 may be configured to compress a portion of housing tube 400, e.g., an application of a force to a portion of housing tube 400 may be configured to compress a portion of first housing tube portion 420. In one or more embodiments, a compression of a portion of housing tube 400 may be configured to gradually curve housing tube 400. Illustratively, a gradual curving of housing tube 400 may be configured to gradually curve optic fiber 450, e.g., from an optic fiber in a first curved position 610 to an optic fiber in a second curved position 620. In one or more embodiments, a line tangent to optic fiber distal end 451 may intersect a line tangent to housing tube proximal end 402 at a second angle, e.g., when optic fiber 450 comprises an optic fiber in a second curved position 620. In one or more embodiments, the second angle may comprise any angle greater than the first angle. For example, the second angle may comprise a 90 degree angle. Illustratively, actuation control 100 and auto-fixing component 520 may be configured to temporarily fix actuation control 100 in a third fixed rotational position within handle inner portion 240. In one or more embodiments, optic fiber 450 may comprise an optic fiber in a second curved position 620, e.g., when actuation control 100 is fixed in the third fixed rotational position within handle inner portion 240.

Figure 6D:
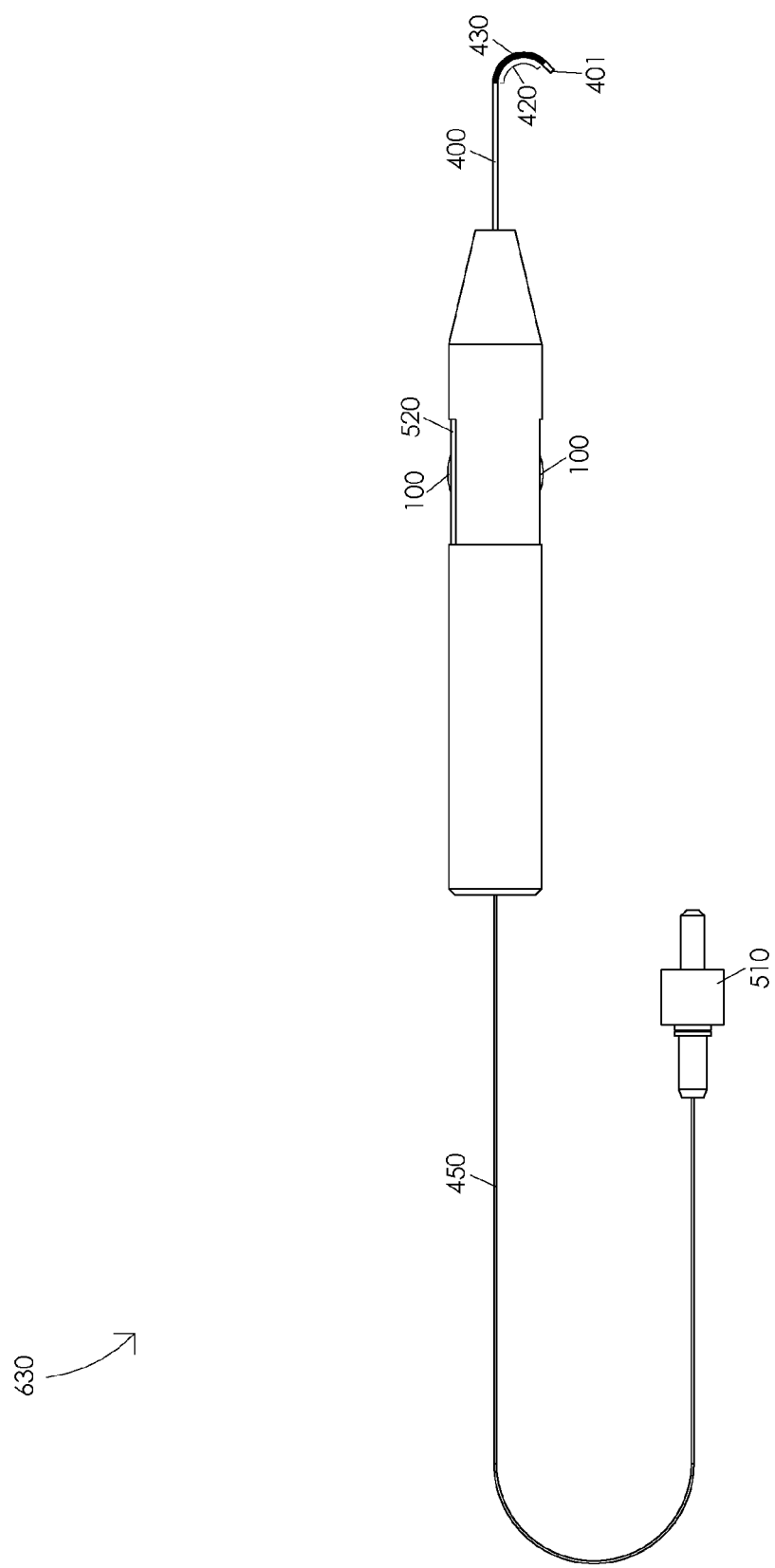

FIG. 6D illustrates an optic fiber in a third curved position 630. In one or more embodiments, a rotation of actuation control 100 within handle inner portion 240 may be configured to gradually curve optic fiber 450 from an optic fiber in a second curved position 620 to an optic fiber in a third curved position 630. Illustratively, a rotation of actuation control 100 within handle inner portion 240 may be configured to retract cable 410 relative to housing tube 400. In one or more embodiments, a refraction of cable 410 relative to housing tube 400 may be configured to apply a force to a portion of housing tube 400, e.g., a retraction of cable 410 relative to housing tube 400 may be configured to apply a force to a portion of first housing tube portion 420. Illustratively, an application of a force to a portion of housing tube 400 may be configured to compress a portion of housing tube 400, e.g., an application of a force to a portion of housing tube 400 may be configured to compress a portion of first housing tube portion 420. In one or more embodiments, a compression of a portion of housing tube 400 may be configured to gradually curve housing tube 400. Illustratively, a gradual curving of housing tube 400 may be configured to gradually curve optic fiber 450, e.g., from an optic fiber in a second curved position 620 to an optic fiber in a third curved position 630. In one or more embodiments, a line tangent to optic fiber distal end 451 may intersect a line tangent to housing tube proximal end 402 at a third angle, e.g., when optic fiber 450 comprises an optic fiber in a third curved position 630. In one or more embodiments, the third angle may comprise any angle greater than the second angle. For example, the third angle may comprise a 135 degree angle. Illustratively, actuation control 100 and auto-fixing component 520 may be configured to temporarily fix actuation control 100 in a fourth fixed rotational position within handle inner portion 240. In one or more embodiments, optic fiber 450 may comprise an optic fiber in a third curved position 630, e.g., when actuation control 100 is fixed in the fourth fixed rotational position within handle inner portion 240.

Figure 6E:
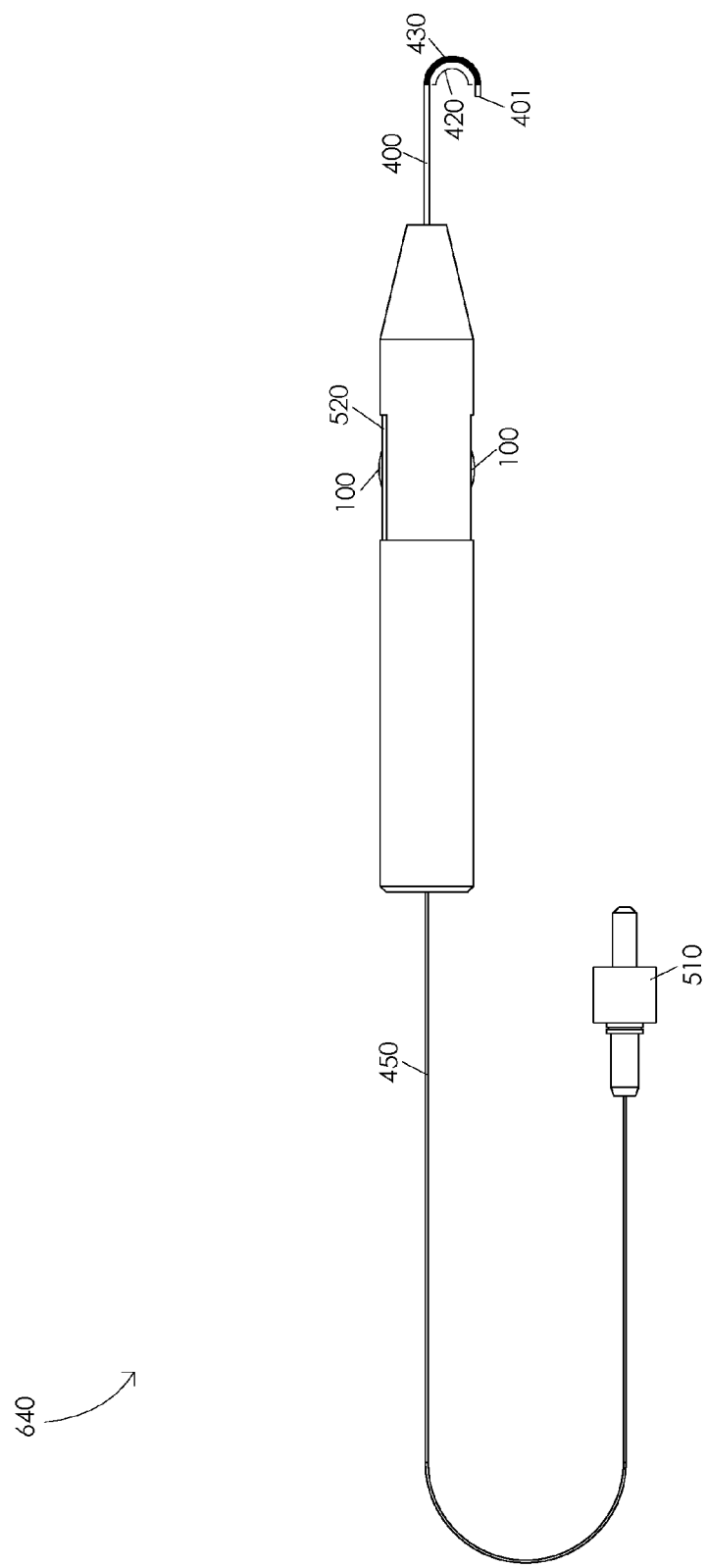

FIG. 6E illustrates an optic fiber in a fourth curved position 640. In one or more embodiments, a rotation of actuation control 100 within handle inner portion 240 may be configured to gradually curve optic fiber 450 from an optic fiber in a third curved position 630 to an optic fiber in a fourth curved position 640. Illustratively, a rotation of actuation control 100 within handle inner portion 240 may be configured to retract cable 410 relative to housing tube 400. In one or more embodiments, a retraction of cable 410 relative to housing tube 400 may be configured to apply a force to a portion of housing tube 400, e.g., a retraction of cable 410 relative to housing tube 400 may be configured to apply a force to a portion of first housing tube portion 420. Illustratively, an application of a force to a portion of housing tube 400 may be configured to compress a portion of housing tube 400, e.g., an application of a force to a portion of housing tube 400 may be configured to compress a portion of first housing tube portion 420. In one or more embodiments, a compression of a portion of housing tube 400 may be configured to gradually curve housing tube 400. Illustratively, a gradual curving of housing tube 400 may be configured to gradually curve optic fiber 450, e.g., from an optic fiber in a third curved position 630 to an optic fiber in a fourth curved position 640. In one or more embodiments, a line tangent to optic fiber distal end 451 may be parallel to a line tangent to housing tube proximal end 402, e.g., when optic fiber 450 comprises an optic fiber in a fourth curved position 640. Illustratively, actuation control 100 and auto-fixing component 520 may be configured to temporarily fix actuation control 100 in a fifth fixed rotational position within handle inner portion 240. In one or more embodiments, optic fiber 450 may comprise an optic fiber in a fourth curved position 640, e.g., when actuation control 100 is fixed in the fifth fixed rotational position within handle inner portion 240.

In one or more embodiments, one or more properties of a steerable laser probe may be adjusted to attain one or more desired steerable laser probe features. Illustratively, a distance that housing tube distal end 401 extends from handle distal end 301 may be adjusted to vary an amount of rotation of actuation control 100 configured to curve housing tube 400 to a particular curved position. In one or more embodiments, a stiffness of first housing tube portion 420 or a stiffness of second housing tube portion 430 may be adjusted to vary an amount of rotation of actuation control 100 configured to curve housing tube 400 to a particular curved position. Illustratively, a material comprising first housing tube portion 420 or a material comprising second housing tube portion 430 may be adjusted to vary an amount of rotation of actuation control 100 configured to curve housing tube 400 to a particular curved position.

In one or more embodiments, a number of apertures in housing tube 400 may be adjusted to vary an amount of rotation of actuation control 100 configured to curve housing tube 400 to a particular curved position. Illustratively, a location of one or more apertures in housing tube 400 may be adjusted to vary an amount of rotation of actuation control 100 configured to curve housing tube 400 to a particular curved position. In one or more embodiments, a geometry of one or more apertures in housing tube 400 may be adjusted to vary an amount of rotation of actuation control 100 configured to curve housing tube 400 to a particular curved position. Illustratively, a geometry of one or more apertures in housing tube 400 may be uniform, e.g., each aperture of the one or more apertures may have a same geometry. In one or more embodiments, a geometry of one or more apertures in housing tube 400 may be non-uniform, e.g., a first aperture in housing tube 400 may have a first geometry and a second aperture in housing tube 400 may have a second geometry. Illustratively, a geometry or location of one or more apertures in housing tube 400 may be optimized to evenly distribute an applied force. For example, a geometry or location of one or more apertures in housing tube 400 may be optimized to evenly distribute a force applied to first housing tube portion 420.

Illustratively, a stiffness of first housing tube portion 420 or a stiffness of second housing tube portion 430 may be adjusted to vary a bend radius of housing tube 400. In one or more embodiments, a stiffness of first housing tube portion 420 or a stiffness of second housing tube portion 430 may be adjusted to vary a radius of curvature of housing tube 400, e.g., when housing tube 400 is in a particular curved position. Illustratively, a number of apertures in housing tube 400 may be adjusted to vary a bend radius of housing tube 400. In one or more embodiments, a number of apertures in housing tube 400 may be adjusted to vary a radius of curvature of housing tube 400, e.g., when housing tube 400 is in a particular curved position. Illustratively, a location or a geometry of one or more apertures in housing tube 400 may be adjusted to vary a bend radius of housing tube 400. In one or more embodiments, a location or a geometry of one or more aperatures in housing tube 400 may be adjusted to vary a radius of curvature of housing tube 400, e.g., when housing tube 400 is in a particular curved position.

In one or more embodiments, at least a portion of optic fiber 450 may be enclosed in an optic fiber sleeve configured to, e.g., protect optic fiber 450, vary a stiffness of optic fiber 450, vary an optical property of optic fiber 450, etc. Illustratively, optic fiber 450 may comprise a buffer, a cladding disposed in the buffer, and a core disposed in the cladding. In one or more embodiments, at least a portion of optic fiber 450 may comprise a buffer configured to protect an optical property of optic fiber 450. Illustratively, at least a portion of optic fiber 450 may comprise a buffer configured to protect an optical layer of optic fiber 450, e.g., the buffer may protect an optical layer of a curved portion of optic fiber 450. In one or more embodiments, at least a portion of optic fiber 450 may comprise a polyimide buffer configured to protect an optical property of optic fiber 450. For example, at least a portion of optic fiber 450 may comprise a Kapton buffer configured to protect an optical property of optic fiber 450.

In one or more embodiments, a location wherein cable 410 may be fixed to housing tube 400 may be adjusted to vary an amount of rotation of actuation control 100 configured to curve housing tube 400 to a particular curved position. For example, a portion of cable 410 may be fixed to an outer portion of housing tube 400. Illustratively, cable 410 may be fixed to housing tube 400 at a plurality of fixation points, e.g., to vary one or more properties of a steerable laser probe. In one or more embodiments, a length of cable 410 may be adjusted to vary an amount of rotation of actuation control 100 configured to curve housing tube 400 to a particular curved position. Illustratively, a steerable laser probe may comprise one or more redundant cables 410. In one or more embodiments, one or more redundant cables 410 may be configured to maintain a particular curved position of housing tube 400, e.g., in the event that cable 410 breaks or fails. Illustratively, one or more redundant cables 410 may be configured to maintain a particular curved position of housing tube 400, e.g., in the event that a cable 410 fixation means fails. In one or more embodiments, one or more redundant cables 410 may be configured to maintain a particular curved position of housing tube 400, e.g., in the event that cable 410 is no longer configured to maintain the particular curved position of housing tube 400. Illustratively, one or more redundant cables 410 may be configured to maintain a particular curved position of housing tube 400 wherein cable 410 is also configured to maintain the particular curved position of housing tube 400.

In one or more embodiments, housing tube 400 may comprise an access window configured to allow access to a portion cable 410. Illustratively, cable 410 may be fixed to a portion of housing tube 400, e.g., by looping a portion of cable 410 through an aperture in housing tube 400. In one or more embodiments, cable 410 may be fixed to a portion of housing tube 400, e.g., by a purely mechanical means. For example, cable 410 may be fixed to a portion of housing tube 400 in a manner other than by an adhesive, a weld, etc. Illustratively, cable 410 may be fixed to a portion of housing tube 400 wherein a portion of cable 410 is configured to fail at a first applied failure force and a fixation means that fixes a portion of cable 410 to a portion of housing tube 400 is configured to fail at a second applied failure force. In one or more embodiments, the second applied failure force may be greater than the first applied failure force.

Illustratively, an arrangement of a portion of cable 410, e.g., an arrangement of a portion of cable 410 between cable distal end 411 and cable proximal end 412, may be adjusted to attain one or more desired steerable laser probe features. In one or more embodiments, an arrangement of a portion of cable 410 may be configured to cause a rotation of actuation control 100, e.g., a rotation of actuation control 100 due to force vector applied to actuation control anterior end 103 and directed towards handle distal end 301 and away from handle proximal end 302, to retract cable 410 relative to housing tube 400. Illustratively, an arrangement of a portion of cable 410 may be configured to cause a rotation of actuation control 100, e.g., a rotation of actuation control 100 due to force vector applied to actuation control anterior end 103 and directed towards handle proximal end 302 and away from handle distal end 301, to extend cable 410 relative to housing tube 400. In one or more embodiments, cable 410 may be disposed within actuation chamber 130, e.g., cable 410 may ingress actuation chamber 130 at actuation control distal end 101, and then disposed within cable housing 120. Illustratively, cable 410 may be disposed within actuation chamber 130, e.g., cable 410 may be disposed over actuation control posterior end 104 and ingress actuation chamber 130 at actuation control proximal end 102, and then disposed within cable housing 120. In one or more embodiments, cable 410 may not be disposed within actuation chamber 130, e.g., cable 410 may be disposed posed over actuation control posterior end 104 and actuation control proximal end 102, and then disposed within cable housing 120.

Illustratively, an arrangement of a portion of cable 410 may be configured to cause a rotation of actuation control 100, e.g., a rotation of actuation control 100 due to force vector applied to actuation control anterior end 103 and directed towards handle proximal end 302 and away from handle distal end 301, to retract cable 410 relative to housing tube 400. In one or more embodiments, an arrangement of a portion of cable 410 may be configured to cause a rotation of actuation control 100, e.g., a rotation of actuation control 100 due to force vector applied to actuation control anterior end 103 and directed towards handle distal end 301 and away from handle proximal end 302, to extend cable 410 relative to housing tube 400. For example, cable 410 may be disposed over a portion of actuation control 100 between actuation control distal end 101 and actuation control anterior end 103, and then disposed within cable housing 120.

Illustratively, a steerable laser probe may be configured to indicate, e.g., to a surgeon, a direction that optic fiber 450 may curve, e.g., due to a rotation of actuation control 100 within handle inner portion 240. In one or more embodiments, a portion of a steerable laser probe, e.g., handle 300, may be marked in a manner configured to indicate a direction that optic fiber 450 may curve. For example, a portion of housing tube 400 may comprise a mark configured to indicate a direction that optic fiber 450 may curve. Illustratively, housing tube 400 may comprise a slight curve, e.g., a curve less than 7.5 degrees, when cable 410 is fully extended relative to housing tube 400. For example, housing tube 400 may comprise a slight curve, e.g., a curve greater than 7.5 degrees, when cable 410 is fully extended relative to housing tube 400. In one or more embodiments, housing tube 400 may comprise a slight curve configured to indicate a direction that optic fiber 450 may curve, e.g., due to a rotation of actuation control 100 within handle inner portion 240.

Figure 7A:
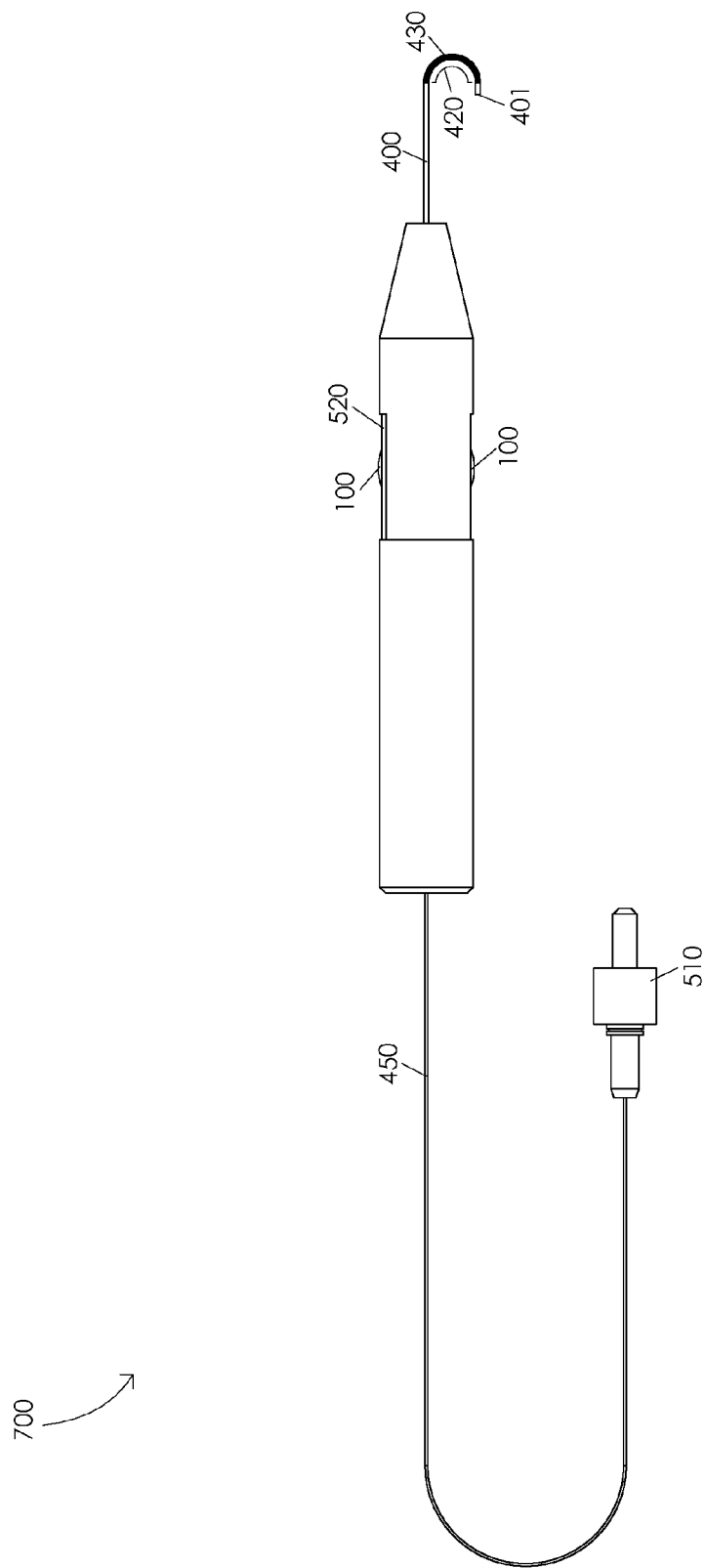

FIGS. 7A, 7B, 7C, 7D, and 7E are schematic diagrams illustrating a gradual straightening of an optic fiber 450. FIG. 7A illustrates a fully curved optic fiber 700. In one or more embodiments, optic fiber 450 may comprise a fully curved optic fiber 700, e.g., when cable 410 is fully retracted relative to housing tube 400. For example, optic fiber 450 may comprise a fully curved optic fiber 700, e.g., when first housing tube portion 420 is fully compressed. In one or more embodiments, a line tangent to optic fiber distal end 451 may be parallel to a line tangent to housing tube proximal end 402, e.g., when optic fiber 450 comprises a fully curved optic fiber 700.

Figure 7B:
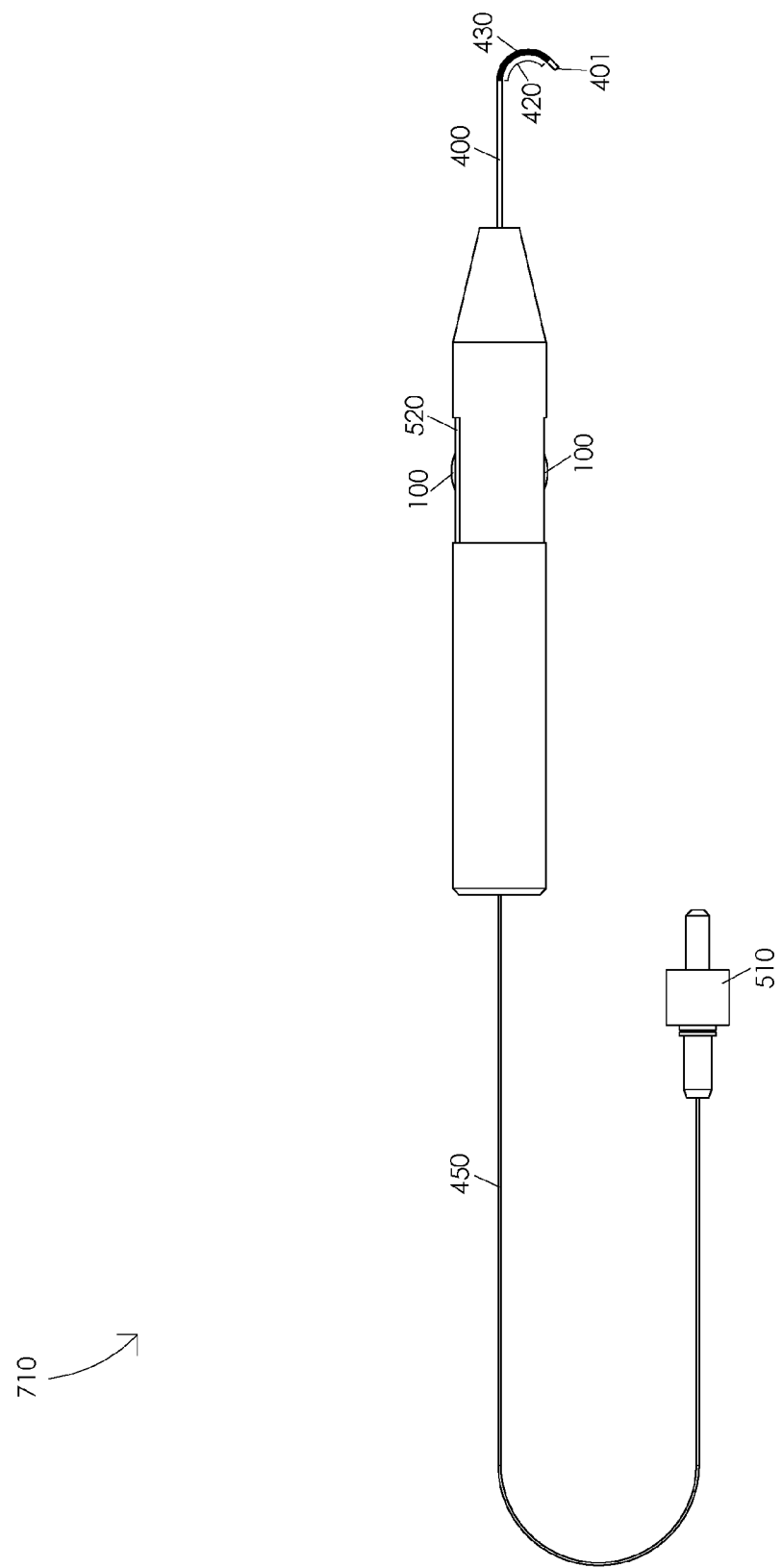

FIG. 7B illustrates an optic fiber in a first partially straightened position 710. In one or more embodiments, a rotation of actuation control 100 within handle inner portion 240 may be configured to gradually straighten optic fiber 450 from a fully curved optic fiber 700 to an optic fiber in a first partially straightened position 710. Illustratively, a rotation of actuation control 100 within handle inner portion 240 may be configured to extend cable 410 relative to housing tube 400. In one or more embodiments, an extension of cable 410 relative to housing tube 400 may be configured to reduce a force applied to housing tube 400, e.g., an extension of cable 410 relative to housing tube 400 may be configured to reduce a force applied to a portion of first housing tube portion 420. Illustratively, a reduction of a force applied to a portion of housing tube 400 may be configured to decompress a portion of housing tube 400, e.g., a reduction of a force applied to a portion of housing tube 400 may be configured to decompress a portion of first housing tube portion 420. In one or more embodiments, a decompression of a portion of housing tube 400 may be configured to gradually straighten housing tube 400. Illustratively, a gradual straightening of housing tube 400 may be configured to gradually straighten optic fiber 450, e.g., from a fully curved optic fiber 700 to an optic fiber in a first partially straightened position 710. In one or more embodiments, a line tangent to optic fiber distal end 451 may intersect a line tangent to housing tube proximal end 402 at a first partially straightened angle, e.g., when optic fiber 450 comprises an optic fiber in a first partially straightened position 710. Illustratively, the first partially straightened angle may comprise any angle less than 180 degrees. For example, the first partially straightened angle may comprise a 135 degree angle.

Figure 7C:
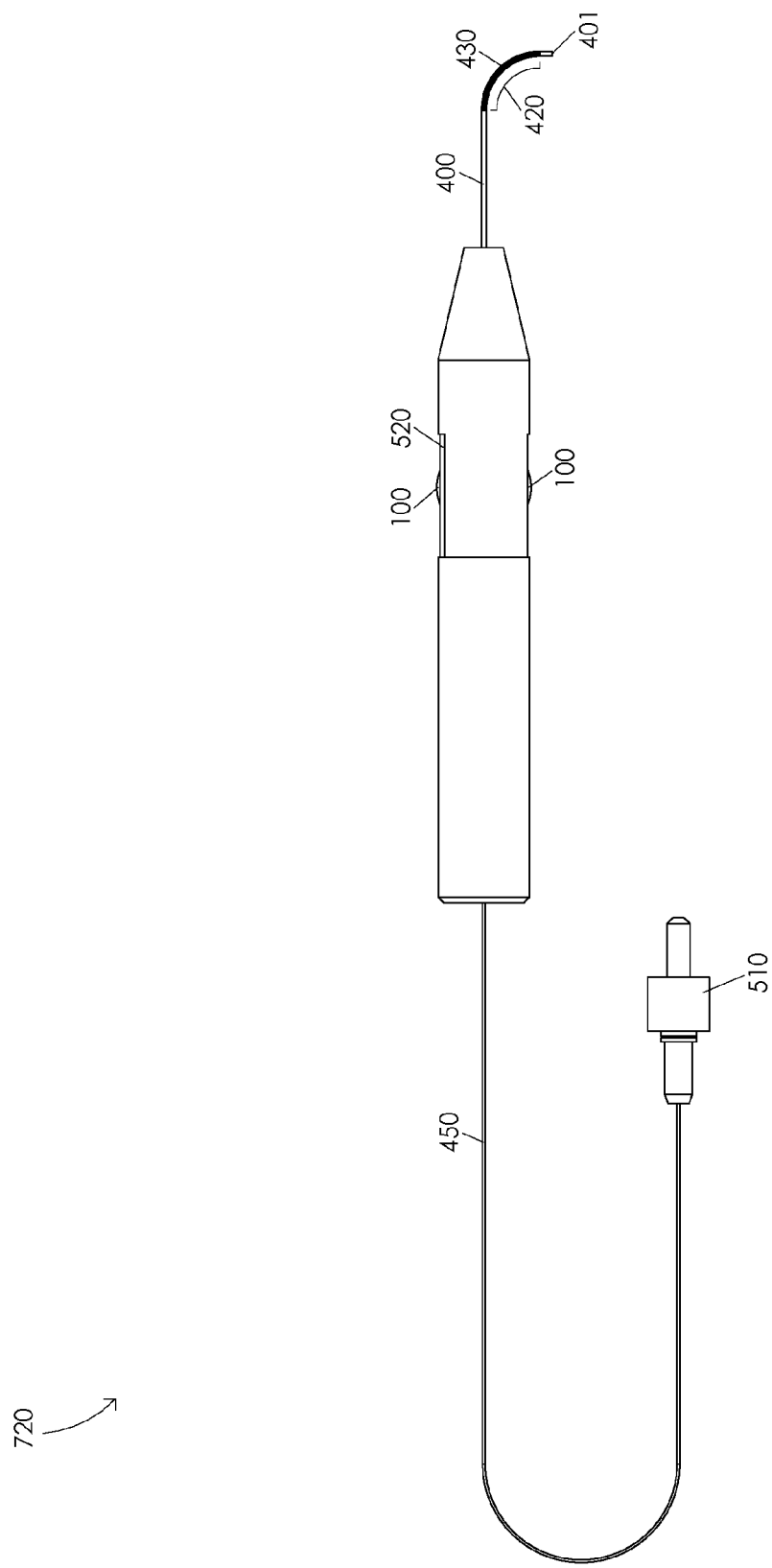

FIG. 7C illustrates an optic fiber in a second partially straightened position 720. In one or more embodiments, a rotation of actuation control 100 within handle inner portion 240 may be configured to gradually straighten optic fiber 450 from an optic fiber in a first partially straightened position 710 to an optic fiber in a second partially straightened position 720. Illustratively, a rotation of actuation control 100 within handle inner portion 240 may be configured to extend cable 410 relative to housing tube 400. In one or more embodiments, an extension of cable 410 relative to housing tube 400 may be con figured to reduce a force applied to housing tube 400, e.g., an extension of cable 410 relative to housing tube 400 may be configured to reduce a force applied to a portion of first housing tube portion 420. Illustratively, a reduction of a force applied to a portion of housing tube 400 may be configured to decompress a portion of housing tube 400, e.g., a reduction of a force applied to a portion of housing tube 400 may be configured to decompress a portion of first housing tube portion 420. In one or more embodiments, a decompression of a portion of housing tube 400 may be configured to gradually straighten housing tube 400. Illustratively, a gradual straightening of housing tube 400 may be configured to gradually straighten optic fiber 450, e.g., from an optic fiber in a first partially straightened position 710 to an optic fiber in a second partially straightened position 720. In one or more embodiments, a line tangent to optic fiber distal end 451 may intersect a line tangent to housing tube proximal end 402 at a second partially straightened angle, e.g., when optic fiber 450 comprises an optic fiber in a second partially straightened position 720. Illustratively, the second partially straightened angle may comprise any angle less than the first partially straightened angle. For example, the second partially straightened angle may comprise a 90 degree angle.

Figure 7D:
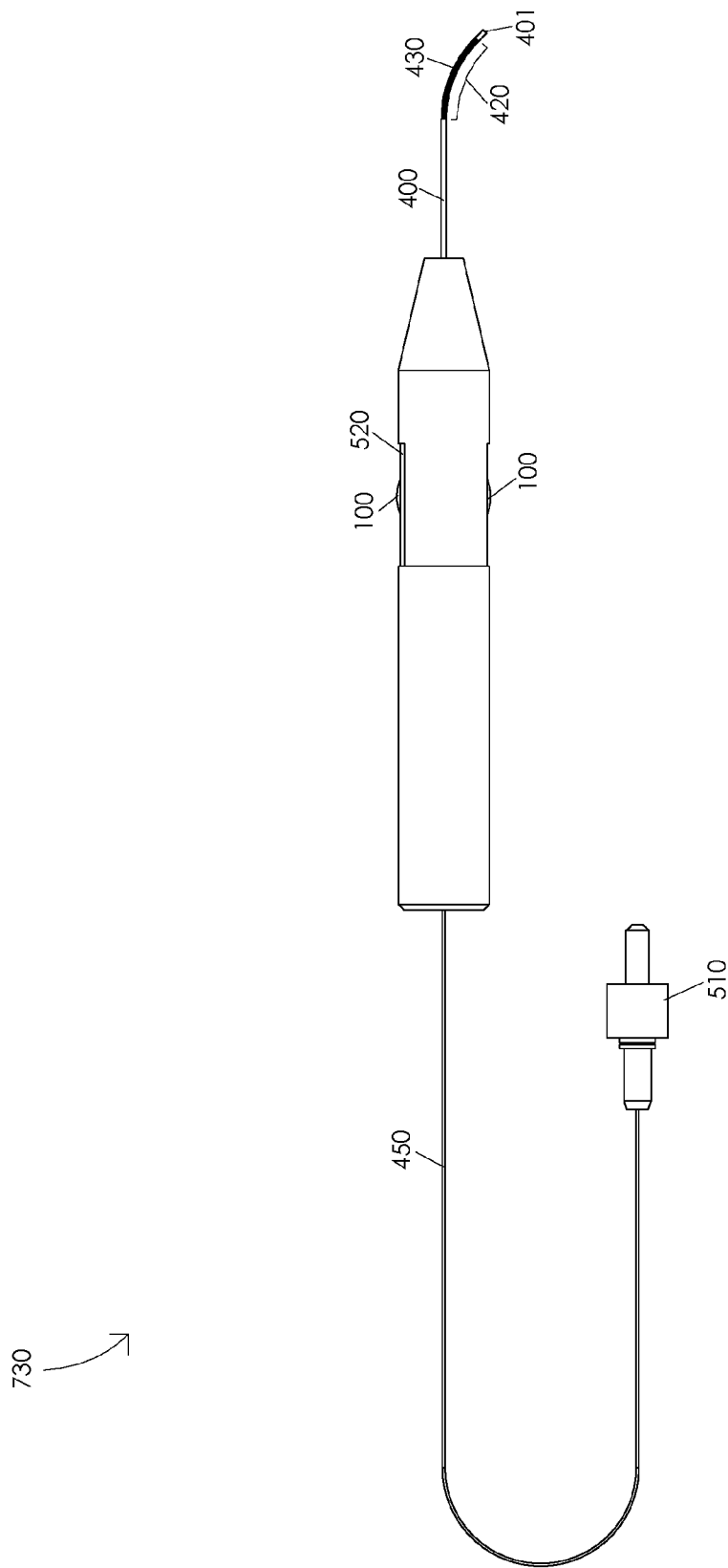

FIG. 7D illustrates an optic fiber in a third partially straightened position 730. In one or more embodiments, a rotation of actuation control 100 within handle inner portion 240 may be configured to gradually straighten optic fiber 450 from an optic fiber in a second partially straightened position 720 to an optic fiber in a third partially straightened position 730. Illustratively, a rotation of actuation control 100 within handle inner portion 240 may be configured to extend cable 410 relative to housing tube 400. In one or more embodiments, an extension of cable 410 relative to housing tube 400 may be configured to reduce a force applied to housing tube 400, e.g., an extension of cable 410 relative to housing tube 400 may be configured to reduce a force applied to a portion of first housing tube portion 420. Illustratively, a reduction of a force applied to a portion of housing tube 400 may be configured to decompress a portion of housing tube 400, e.g., a reduction of a force applied to a portion of housing tube 400 may be configured to decompress a portion of first housing tube portion 420. In one or more embodiments, a decompression of a portion of housing tube 400 may be configured to gradually straighten housing tube 400. Illustratively, a gradual straightening of housing tube 400 may be configured to gradually straighten optic fiber 450, e.g., from an optic fiber in a second partially straightened position 720 to an optic fiber in a third partially straightened position 730. In one or more embodiments, a line tangent to optic fiber distal end 451 may intersect a line tangent to housing tube proximal end 402 at a third partially straightened angle, e.g., when optic fiber 450 comprises an optic fiber in a third partially straightened position 730. Illustratively, the third partially straightened angle may comprise any angle less than the second partially straightened angle. For example, the third partially straightened angle may comprise a 45 degree angle.

FIG. 7E illustrates an optic fiber in a fully straightened position 740. In one or more embodiments, a rotation of actuation control 100 within handle inner portion 240 may be configured to gradually straighten optic fiber 450 from an optic fiber in a third partially straightened position 730 to an optic fiber in a fully straightened position 740. Illustratively, a rotation of actuation control 100 within handle inner portion 240 may be configured to extend cable 410 relative to housing tube 400. In one or more embodiments, an extension of cable 410 relative to housing tube 400 may be configured to reduce a force applied to housing tube 400, e.g., an extension of cable 410 relative to housing tube 400 may be configured to reduce a force applied to a portion of first housing tube portion 420. Illustratively, a reduction of a force applied to a portion of housing tube 400 may be configured to decompress a portion of housing tube 400, e.g., a reduction of a force applied to a portion of housing tube 400 may be configured to decompress a portion of first housing tube portion 420. In one or more embodiments, a decompression of a portion of housing tube 400 may be configured to gradually straighten housing tube 400. Illustratively, a gradual straightening of housing tube 400 may be configured to gradually straighten optic fiber 450, e.g., from an optic fiber in a third partially straightened position 730 to an optic fiber in a fully straightened position 740. In one or more embodiments, a line tangent to optic fiber distal end 451 may be parallel to a line tangent to housing tube proximal end 402, e.g., when optic fiber 450 comprises an optic fiber in a fully straightened position 740.

Illustratively, a surgeon may aim optic fiber distal end 451 at any of a plurality of targets within an eye, e.g., to perform a photocoagulation procedure, to illuminate a surgical target site, etc. In one or more embodiments, a surgeon may aim optic fiber distal end 451 at any target within a particular transverse plane of the inner eye by, e.g., rotating handle 300 to orient housing tube 400 in an orientation configured to cause a curvature of housing tube 400 within the particular transverse plane of the inner eye and varying an amount of rotation of actuation control 100 within handle inner portion 240. Illustratively, a surgeon may aim optic fiber distal end 451 at any target within a particular sagittal plane of the inner eye by, e.g., rotating handle 300 to orient housing tube 400 in an orientation configured to cause a curvature of housing tube 400 within the particular sagittal plane of the inner eye and varying an amount of rotation of actuation control 100 within handle inner portion 240. In one or more embodiments, a surgeon may aim optic fiber distal end 451 at any target within a particular frontal plane of the inner eye by, e.g., varying an amount of rotation of actuation control 100 within handle inner portion 240 to orient a line tangent to optic fiber distal end 451 wherein the line tangent to optic fiber distal end 451 is within the particular frontal plane of the inner eye and rotating handle 300. Illustratively, a surgeon may aim optic fiber distal end 451 at any target located outside of the particular transverse plane, the particular sagittal plane, and the particular frontal plane of the inner eye, e.g., by varying a rotational orientation of handle 300 and varying an amount of rotation of actuation control 100 within handle inner portion 240. In one or more embodiments, a surgeon may aim optic fiber distal end 451 at any target of a plurality of targets within an eye, e.g., without increasing a length of a portion of a steerable laser probe within the eye. Illustratively, a surgeon may aim optic fiber distal end 451 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
    a handle having a handle distal end and a handle proximal end;
    a handle end cap of the handle having a handle end cap distal end and a handle end cap proximal end;
    a handle base of the handle having a handle base distal end and a handle base proximal end;
    an actuation control mount of the handle having an actuation control mount distal end and an actuation control mount proximal end wherein the actuation control mount distal end is disposed in the handle base and wherein the actuation control mount proximal end is disposed in the handle end cap;
    an actuation control of the handle having an actuation control distal end, an actuation control proximal end, an actuation control anterior end, and an actuation control posterior end, the actuation control disposed within the actuation control mount wherein an application of a first force vector directed towards the handle distal end and away from the handle proximal end to the actuation control anterior end is configured to rotate the actuation control in a first direction and wherein an application of a second force vector directed towards the handle proximal end and away from the handle distal end to the actuation control anterior end is configured to rotate the actuation control in a second direction;
    an actuation chamber disposed in the actuation control, the actuation chamber extending completely from the actuation control distal end to the actuation control proximal end;
    a housing tube having a housing tube distal end and a housing tube proximal end, the housing tube having dimensions configured to perform microsurgical procedures; and
    an optic fiber having an optic fiber distal end and an optic fiber proximal end, the optic fiber disposed in the housing tube, an inner portion of the handle, and the actuation chamber wherein a geometry of the actuation chamber is configured to prevent a contact between a portion of the actuation control and a portion of the optic fiber due to a rotation of the actuation control and wherein the optic fiber distal end is adjacent to the housing tube distal end.

2. The instrument of claim 1 wherein a rotation of the actuation control in the first direction is configured to curve the optic fiber.

3. The instrument of claim 2 wherein the rotation of the actuation control in the first direction is configured to curve the optic fiber at least 45 degrees relative to the housing tube proximal end.

4. The instrument of claim 2 wherein the rotation of the actuation control in the first direction is configured to curve the housing tube.

5. The instrument of claim 1 wherein a rotation of the actuation control in the first direction is configured to straighten the optic fiber.

6. The instrument of claim 5 wherein the rotation of the actuation control in the first direction is configured to straighten the optic fiber at least 45 degrees relative to the housing tube proximal end.

7. The instrument of claim 5 wherein the rotation of the actuation control in the first direction is configured to straighten the housing tube.

8. The instrument of claim 1 wherein a rotation of the actuation control in the second direction is configured to curve the optic fiber.

9. The instrument of claim 8 wherein the rotation of the actuation control in the second direction is configured to curve the optic fiber at least 45 degrees relative to the housing tube proximal end.

10. The instrument of claim 8 wherein the rotation of the actuation control in the second direction is configured to curve the housing tube.

11. The instrument of claim 1 wherein a rotation of the actuation control in the second direction is configured to straighten the optic fiber.

12. The instrument of claim 11 wherein the rotation of the actuation control in the second direction is configured to straighten the optic fiber at least 45 degrees relative to the housing tube proximal end.

13. The instrument of claim 11 wherein the rotation of the actuation control in the second direction is configured to straighten the housing tube.

14. The instrument of claim 1 further comprising:
    an auto-fixing component of the handle.

15. The instrument of claim 14 wherein the auto-fixing component is configured to temporarily fix the actuation control in a first rotational position in the first direction.

16. The instrument of claim 15 wherein temporarily fixing the actuation control in the first rotational position in the first direction is configured to temporarily fix the optic fiber in a first curved position relative to the housing tube proximal end.

17. The instrument of claim 16 wherein the auto-fixing component is configured to temporarily fix the actuation control in a second rotational position in the first direction and wherein temporarily fixing the actuation control in the second rotational position in the first direction is configured to temporarily fix the optic fiber in a second curved position relative to the housing tube proximal end.

18. The instrument of claim 14 wherein the auto-fixing component is configured to temporarily fix the actuation control in a first rotational position in the second direction.

19. The instrument of claim 18 wherein temporarily fixing the actuation control in the first rotational position in the second direction is configured to temporarily fix the optic fiber in a first curved position relative to the housing tube proximal end.

20. The instrument of claim 19 wherein the auto-fixing component is configured to temporarily fix the actuation control in a second rotational position in the second direction and wherein temporarily fixing the actuation control in the second rotational position in the second direction is configured to temporarily fix the optic fiber in a second curved position relative to the housing tube proximal end.

\* \* \* \* \*